United States Patent
Chang et al.

(10) Patent No.: US 6,900,036 B2
(45) Date of Patent: May 31, 2005

(54) PRION ISOMERS, METHODS OF MAKING, METHODS OF USING, AND COMPOSITIONS AND PRODUCTS COMPRISING PRION ISOMERS

(75) Inventors: Jui-Yoa Chang, Houston, TX (US); Bao-Yuan Lu, Houston, TX (US)

(73) Assignee: University of Texas Health Science Center Houston, Houston, TX (US)

( * ) Notice: Subject to any disclaimer, the term of this patent is extended or adjusted under 35 U.S.C. 154(b) by 0 days.

(21) Appl. No.: 10/025,976

(22) Filed: Dec. 19, 2001

(65) Prior Publication Data

US 2002/0132268 A1 Sep. 19, 2002

Related U.S. Application Data

(60) Provisional application No. 60/258,576, filed on Dec. 27, 2000.

(51) Int. Cl.[7] .................. C12P 21/04; A61K 49/00; A61K 39/395

(52) U.S. Cl. .................. 435/70.1; 424/9.1; 424/9.2; 424/130.1; 424/184.1; 424/192.1; 435/71.1; 530/300; 530/350

(58) Field of Search .................. 424/184.1, 192.1, 424/9.1, 130.1; 435/70.1, 71.1; 530/300, 350

*Primary Examiner*—Rodney P Swartz
(74) *Attorney, Agent, or Firm*—Gilbreth & Associates, P.C.; J. M. Gilbreth; Mary A. Gilbreth

(57) ABSTRACT

Prion peptides exhibiting structural isomerism to wild-type prion peptide are disclosed. The invention further discloses methods of making prion isomers, compositions comprising prion isomers, and compositions and products comprising antibody to a prion isomer. Methods for screening a patient for a neuro-degenerative disease, and methods for treating a patient afflicted with a neuro-degenerative disease are also disclosed.

31 Claims, 12 Drawing Sheets

BUFFER ALONE

1M UREA

2M UREA

4M UREA

6M UREA

8M UREA

RP-HPLC

SEC

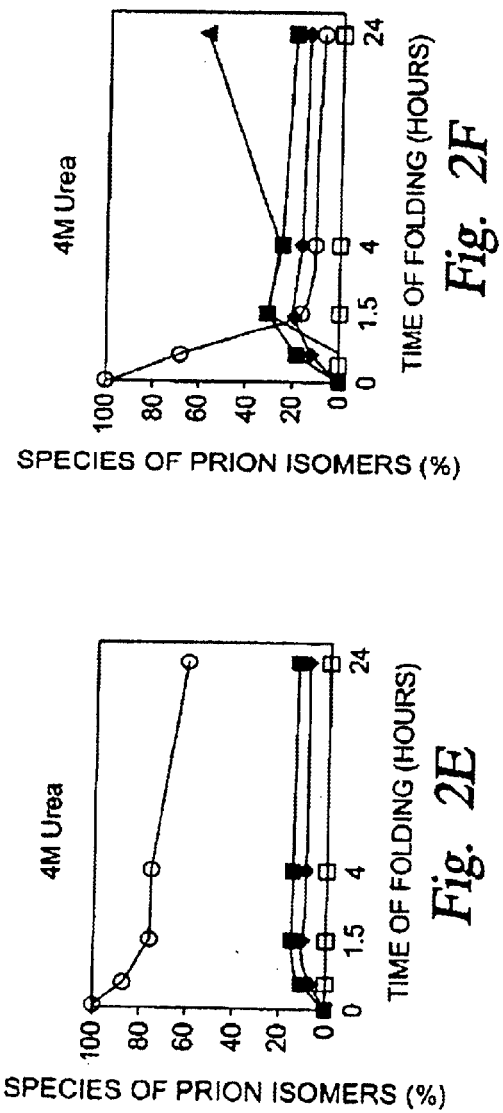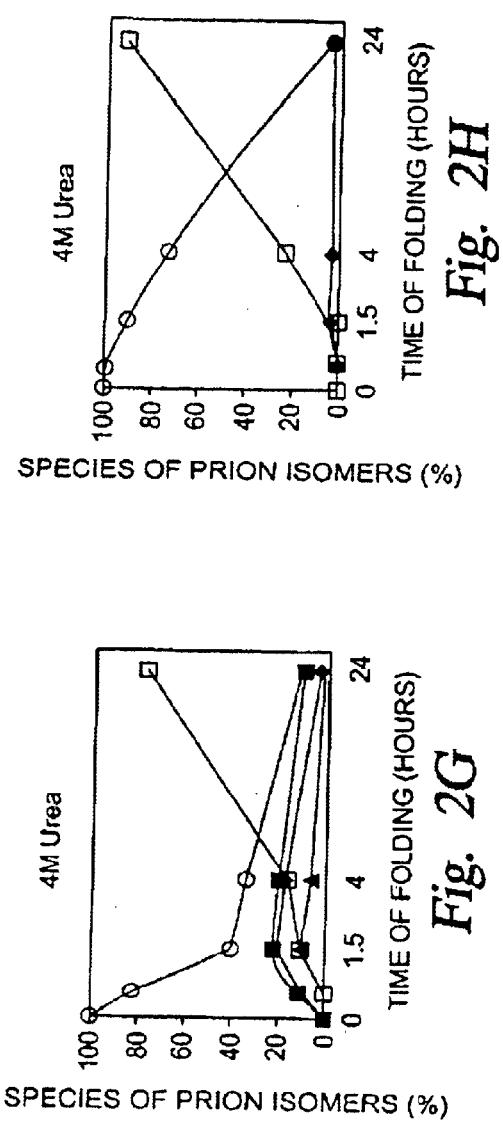

6 M GdmCl at pH 8.0

8 M Urea at pH 8.0

PRION ISOMERS, METHODS OF MAKING, METHODS OF USING, AND COMPOSITIONS AND PRODUCTS COMPRISING PRION ISOMERS

RELATED APPLICATION DATA

This application claims priority of U.S. Provisional Application, Serial No. 60/258,576, filed Dec. 27, 2000.

BACKGROUND OF THE INVENTION

1. Field of the Invention

The present invention relates to prion isomers, referred to herein as PrPI. In another aspect, the present invention relates to methods of making prion isomers. In even another aspect, the present invention relates to compositions comprising a prion isomer peptide, and to methods of making said compositions. In still another aspect, the present invention relates to antibodies having specificity to at least one prion isomer, and to methods of making said antibodies. In yet another aspect, the present invention relates to products useful for assaying for the presence of prion isomers in a patient, and to methods of using said products. In even still another aspect, the present invention is directed to methods for treating a patient afflicted with a prion-associated disorder.

2. Description of the Related Art

Prions are infectious pathogens distinct from bacteria, viruses and viroids, and cause central nervous system spongiform encephalopathies in humans and animals. Examples of prion diseases include the mad cow disease, scrapie in sheep, and the human diseases Creutzfledt-Jacob disease, Gerstmann-Straussler-Scheinker disease, familial insomnia, and kuru (Gajdusek, 1977; Prusiner, 1997 and 1999; Weissmann and Aguzzi, 1997; Hill et al., 1997; Will et al., 1999). Thus, prion diseases are neuro-degenerative diseases that afflict both humans and animals.

Research indicates that prion diseases develop by a "protein only" mechanism (Griffith, 1967; Prusiner, 1982; Cohen and Prusiner, 1998; Balter,1999). The predominant hypothesis at present is that no nucleic acid component is necessary for infectivity of prion protein. The underlying cause of prion disease is the conversion of a host derived cellular prion (PrPC) into an infectious scrapie prion (PrPSC) (Prusiner 1997 and 1999; Cohen and Prusiner, 1998; Horiuchi and Caughey, 1999). Interestingly, the PrPC and PrPSC proteins have the same molecular weight and amino acid sequences (Stahl et al., 1993) and differ only in their three-dimensional conformations.

The conformational difference between the non-infectious PrPC protein and the infectious PrPSC protein is associated with considerable dissimilarity of the physicochemical properties of the proteins. Unlike the PrPC protein, which is soluble, susceptible to enzyme digestion and rich in α-helical structure, the PrPSC protein is highly insoluble, partially resistant to proteolytic digestion and possesses a high content of β-sheet structure (Prusiner, 1999; Cohen and Prusiner, 1998; Jackson et al., 1999).

The PrPC protein is a sialoglycoprotein encoded by a gene that is located on human chromosome 20 (Oesch, B. et al., Cell 40:735–746, (1985); Basler, K. et al., 46:417–428 (1986); Liao, Y. J. et al., Science 233:364–367 (1986); Meyer, R. K. et al., Proc. Natl. Acad. Sci. USA 83:2310–2314 (1986); Sparkes, R. S. et al., Proc. Natl. Acad. Sci. USA 83:7358–7362 (1986); Bendheim, P. E. et al. J. Infect. Dis. 158:1198–1208 (1988); Turk, E. et al. Eur. J. Biochem. 176:21–30 (1988)). The PrP gene is expressed in neural and non-neural tissues, the highest concentration of mRNA being in neurons (Chesebro, B. et al., Nature 315:331–333 (1985); Kretzschmar, H. A. et al., Am. J. Pathol. 122:1–5 (1986); Brown, H. R. et al., Acta Neuropathol. 80:1–6 (1990); Cashman, N. R. et al., Cell 61:185–192 (1990); Bendheim, P. E., Neurology 42:149–156 (1992)). The translation product of PrP gene consists of 253 amino acids in humans (Kretzschmar, H. A. et al., DNA 5:315–324 (1986); Pucket, C. et al., Am. J. Hum. 49:320–329 (1991)), 254 in hamster and mice, and 256 amino acids in sheep. The PrP protein undergoes several post-translational modifications.

To date, the majority of prion structural data has been obtained by analyzing the structure of PrPC. The three-dimensional structures of mouse PrPC proteins of various lengths were determined by NMR analyses (Riek et al., 1996 and 1997; James et al., 1997; Donne et al., 1997; Daggett, 1998). Such analyses revealed that the protein contains three well-resolved α-helices and a short two-stranded β-sheets. PrPC contains one disulfide bond, is structurally plastic and may exist in various conformations under different conditions (Prusiner et al., 1993; Cohen and Prusiner, 1998). Attempts at investigating the structure of PrPSC have, unfortunately, been hampered by its intractable solubility.

Numerous efforts have been aimed at searching for conditions that generate prion isomers with an increased content of β-sheet structure, as well as PrPSC characteristics, in hopes of obtaining models with which PrP pathogenicity can be studied.

A scrapie-like prion rich in β-sheet structure was found to exist as a PrPC unfolding intermediate at pH 4.0 in the presence of 3.5 M urea (Hornemann and Glockshuber, 1998). A PrPC unfolding intermediate is also observed at pH 3.6–4.0 under 1–2M GdmCl (Swietnicki et al., 1997, 1998 and 2000; Zhang et al., 1997). Additionally, reduction of the disulfide bond in the presence of dithiothreitol (100 mM) and 6M GdmCl is capable of converting PrPC to a structure that exhibits high β-sheet content, is prone to aggregation and resistant to proteinase K (Jackson et al., 1999). Synthetic fragments of PrPC have also been shown to adopt β-rich conformations and to form amyloid, but these synthetic PrPC fragments fail to cause disease in rodents (Gasset et al., 1992). Cell-free induction of protease resistant prion in the presence of preexisting PrPSC has also been demonstrated (Kocisko et al., 1994; Caughey et al., 1999).

In spite of advancements in the art, conditions that permit fractionation and isolation of stable prion isomers have not been demonstrated. Thus, there remains a need for stable PrPSC-like prion peptides that are conformational isomers of PrPC wherein the isomers are useful as models for better understanding protein folding, prion pathogenicity, and prion-associated neuro-degenerative disorders.

There is another need in the art for methods of making said novel conformational isoforms of the prion protein.

There is even another need in the art for compositions comprising a peptide of a novel prion isoform useful in understanding and treating prion-associated disorders, and for methods of making such compositions.

There is still another need in the art for antibodies specific to prion isoforms useful for screening and/or treating a patient afflicted with a prion-associated disorder, preferably a neuro-degenerative disorder, and for methods of making such antibodies.

There is yet another need in the art for compositions comprising antibodies specific to prion isoforms useful for treating a patient afflicted with a prion-associated disorder, preferably a neuro-degenerative disorder, and for methods of making such compositions.

There is even still another need in the art for products comprising an antibody having specificity to at least one prion isomer.

There is even yet another need in the art for methods of detecting prion isomers in a patient.

There is still even another need in the art for methods of treating a patient afflicted with a prion-associated disorder, preferably a neuro-degenerative disorder.

These and other needs will become apparent to those of skill in the art upon review of this specification, including its drawings, claims and appendix.

SUMMARY OF THE INVENTION

It is an object of the present invention to provide novel conformational isoforms of prion peptides and prion protein.

It is another object of the present invention to provide methods for making novel conformational isoforms of the prion protein.

It is even another object of the present invention to provide compositions useful in understanding and treating prion-associated neuro-degenerative disorders, wherein the compositions comprise a prion isoform peptide.

It is still another object of the present invention to provide antibodies useful for treating a patient afflicted with a prion-associated disorder, preferably a neuro-degenerative disorder, wherein the antibodies have specificity to at least one prion isoform, and to methods of making such antibodies.

It is yet another object of the present invention to provide compositions comprising an antibody having specificity to a prion isoform wherein the compositions are useful in treating a patient afflicted with a prion-associated disorder, preferably a neuro-degenerative disorder, and methods of making such compositions.

It is even still another object of the present invention to provide products comprising an antibody having specificity to at least one prion isomer.

It is even yet another object of the present invention to provide methods of detecting prion isomers in a patient.

It is still even another object of the present invention to provide methods of treating a patient afflicted with a prion-associated disorder, preferably a neuro-degenerative disorder.

According to one embodiment of the present invention there is provided a prion isomer comprising at least a portion of a prion peptide. Preferably, the isomer has a three-dimensional conformation isomeric to the three-dimensional conformation of a wild-type prion peptide of equivalent amino acid sequence. In general these prion isomers are referred to herein as PrPI, and specific isomers herein are referred to as PrP-R, PrP-a, PrP-b, PrP-c and PrP-Z.

According to another embodiment of the present invention there is provided a method for making a prion isomer. Generally the method comprises the step of incubating a prion peptide in a reducing buffer (also referred to as a denaturing buffer) in order to produce a reduced prion peptide. The method further comprises incubating the reduced prion peptide in an isomerization buffer in order to produce a PrPI isomeric peptide.

According to even another embodiment of the present invention there is provided a composition comprising a prion peptide wherein the prion peptide is isomeric to a wild type prion protein.

According to still another embodiment of the present invention there is provided a sequence encoding an antibody having affinity to a structural isomer of a wild-type prion peptide.

According to yet another embodiment of the present invention there is provided a composition comprising an antibody having affinity to a structural isomer of a wild-type prion isomer.

According to even still another embodiment of the present invention there is provided a method for treating a patient. Generally the method comprises administering an effective dose of a composition to a patient, wherein the composition comprises an having specific affinity to a PrPI isomer.

These and other embodiments of the present invention will become apparent to those of skill in the art upon review of this specification, including its drawings, appendix, and claims.

DETAILED DESCRIPTION OF THE INVENTION

Figure 1A:
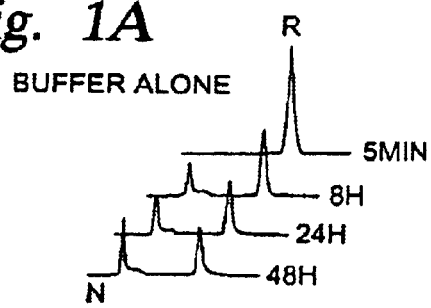
FIG. 1 depicts HPLC results of folding of a reduced murine prion, mPrP(23-231), in the presence of different urea concentrations at a pH of 4.0.
Figure 1B:
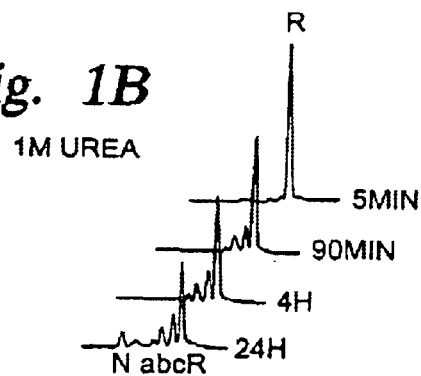
Figure 1C:
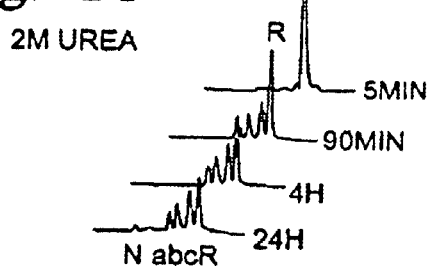
Figure 1D:
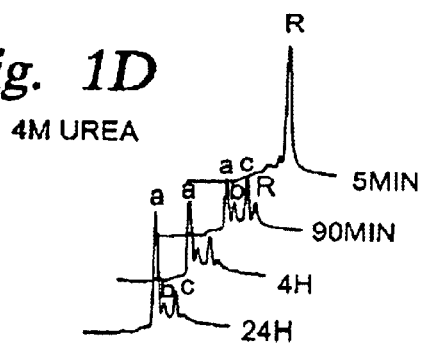
Figure 1E:
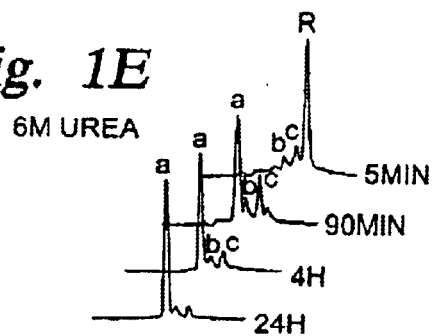
Figure 1F:
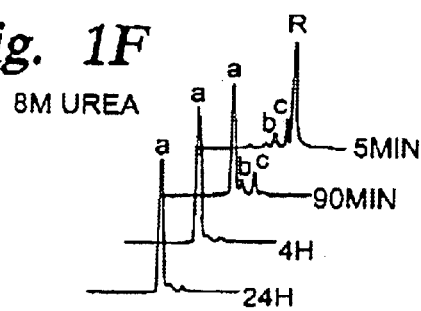

The present invention is directed to the production, isolation and utilization of prion isomer peptides and proteins, referred to hereinafter as PrPI, and to products and methods utilizing PrPI. The PrPI isomers of the invention generally are stable in reduced form, exhibit a high content of β-sheet structure, and exhibit characteristics of the pathogenic prion, PrPSC. Such PrPSC characteristics include, for example, being prone to formation of aggregates, having lower solubility in comparison to PrPC, having a higher content of β-sheet structure in comparison to PrPC. Some PrPIs of the invention may also be more resistant to proteolytic degradation in comparison to PrPC. The prion peptide isoforms of the present invention generally comprise any portion of any prion sequence, wherein the sequence may be the wild-type sequence or a mutant sequence. Preferably the prion sequence is a mammalian prion sequence, more preferably a human prion sequence. Prion sequences are known in the art and are can be found in the literature including the references cited herein which are incorporated herein by reference, and in databases such as, for example, GenBank, as is known by one of ordinary skill in the art. All such prion sequences are included herein.

According to one embodiment of the invention there is provided a prion isomer. The isomers of the invention have no restrictions on their size and thus may consist of any portion of the full-length prion protein or may be the full-length prion protein sequence. The isomers of the invention may comprise any multiple of the full-length prion protein or any multiple of any portion of the prion protein. These latter isomers are referred to herein as polymers and/or aggregates.

By definition, the isomers of the invention have a three-dimensional conformation that is isomeric to the three-dimensional conformation of a wild-type prion peptide of an equivalent amino acid sequence. The PrPIs of the invention may be in purified, partially purified, or non-purified form. All techniques known in the art for isolating, purifying and concentrating peptides and proteins, such as, for example, those discussed in Hornemann S. et al., (1997), *FEBS Lett.* 413, 277–281; Maniatis T. et al., "Molecular Cloning, a Laboratory Manual", Cold Spring Harbor Laboratory, Cold Spring Harbor, N.Y., 1982; Ausubel F. M. et al. (eds); and "Current Protocols in Molecular Biology", John Wiley & Sons, New York, (1987) are suitable for use with the PrPI herein and are incorporated herein by reference.

Generally, the PrPI isomers of the invention comprise a greater proportion of β-sheet sub-structures in comparison to the structure of the wild-type prion protein, PrPC. In addition, some of the PrPI isomers may be more resistant to proteolytic digestion in comparison to PrPC, and may be less soluble than PrPC.

Analyses for determining various properties of PrPI peptides of the invention are well known in the art. For example, content of β-sheet sub-structure may be analyzed by determining far-UV circular dichroism spectra, and resistance to proteolytic degradation may be determined by incubation of the peptide together with a protease under proper reaction conditions. Any and all analytical techniques known in the art, for example those discussed in J. Y. Chang and B. Y. Lu, Appendix A; Maniatis T. et al., "Molecular Cloning, a Laboratory Manual", Cold Spring Harbor Laboratory, Cold Spring Harbor, N.Y., 1982; Ausubel F. M. et al. (eds); and "Current Protocols in Molecular Biology", John Wiley & Sons, New York, (1987) are appropriate for use in analyzing PrPI peptides and proteins of the invention and are incorporated herein by reference.

The peptide sequences of the invention may be any prion sequence, such as, for example, yeast, mouse, sheep, cow, and human PrP. In a preferred embodiment, the prion sequence is a mammalian sequence. In a more preferred embodiment, the prion sequence is a human sequence.

Another embodiment of the invention is directed to a method for making a prion isomer. Generally the method of the invention comprises the step of incubating a composition comprising at least one species of prion peptide in a reducing buffer (also referred to as a denaturing buffer) in order to produce a reduced prion peptide. The method further comprises incubating the reduced prion peptide in a isomerization buffer (also referred to as a folding buffer, or a polymerizing buffer) to produce a PrPI isomeric peptide. Preferably, the resulting PrPI isomeric peptide will have a conformation that is isomeric to the conformation of a PrPC of equivalent amino acid sequence. The resulting prion isomers are stable conformational isomers that can be separated and isolated by HPLC utilizing acidic conditions.

The isomerization buffer utilized herein generally comprises urea or GdmCl. For those isomerization buffers comprising urea, generally the urea concentration is in the range of about 0.1M to 10M and at a pH in the range of about 1.0 to about 6.0. Preferably the urea concentration is in the range of about 1M to about 9.0M and a pH in the range of about 1.5 to about 5.0. One particularly preferred urea-containing isomerization buffer useful in the present invention comprises a urea concentration of about 4.0 M and a pH of about 4.0. Another particularly preferred urea-containing isomerization buffer useful in the present invention comprises a urea concentration in the range of about 6.0 to about 8.0 M urea and a pH of about 4.0.

For isomerization buffers comprising GdmCl, generally the GdmCl concentration is in the range of about 0.1M to about 10M. Preferably the GdmCl is at a concentration in the range of about 0.25M to about 6.0M, more preferably in the range of about 0.5M to about 4.0M. In a particularly preferred embodiment the GdmCl isomerization buffer comprises GdmCl at a concentration of about 2M. The pH of the GdmCl-containing isomerization buffer is generally in the range of about 1.0 to about 6.0, preferably about 2.0 to about 5.5, more preferably about 2.0 to about 5.0. In a particularly preferred embodiment, the GdmCl-containing isomerization buffer has a pH of about 4.0.

Generally the folding reaction is allowed to proceed for a time period ranging from about 30 seconds to about 48 hours, preferably from about 1 minute to about 36 hours, more preferably from about 2 minutes to about 30 hours, most preferably from about 4 minutes to about 28 hours. In a particularly preferred embodiment, the folding reaction is carried out for about 3.5 hours to about 24 hours.

The folding reaction is generally performed at a temperature in the range of about 0° C. to about 60° C., preferably in the range of about 10° C. to about 50° C., more preferably in the range of about 15° C. to about 40° C. In a particularly preferred embodiment, the folding reaction is carried out at a temperature of about 20° C. to about 25° C.

The prion peptides utilized herein may be from any source. Techniques for expressing and purifying recombinant proteins and peptides are well known in the art and all such techniques, for example, those discussed in S. Hornemann et al., (1997), *FEBS Lett.* 413, 277–281; Maniatis T. et al., "Molecular Cloning, a Laboratory Manual", Cold Spring Harbor Laboratory, Cold Spring Harbor, N.Y., 1982; Ausubel F. M. et al. (eds); and "Current Protocols in Molecular Biology", John Wiley & Sons, New York, (1987) may be used in the present invention and are incorporated herein by reference. Thus, the prion sequence utilized in the invention may be expressed from any expression vector known in the art. Suitable vectors known in the art include, for example, bacterial expression vectors, yeast expression vectors, eukaryotic expression vectors, and viral vectors.

In principle, all vectors which replicate and express the desired sequence according to the invention in the chosen host are suitable. Examples of vectors which are suitable for the expression in an *E. coli* strain are bacteriophages, for example derivatives of lambda or M13 bacteriophages, or plasmids, such as, the plasmid ColE1 and its derivatives, for example pMB9, pSF2124, pBR317 or pBR322. A preferred vector of the present invention is pRBI-PDI-T7.

Even another embodiment of the invention is directed to compositions. The compositions of the invention generally comprise an antibody having affinity to a structural isomer of a wild-type prion isomer. These compositions comprising a PrPI antibody are useful in screening and/or treating a patient having a neurological disease. Alternatively, compositions of the invention may comprise a PrPI peptide of the invention wherein the PrPI peptide has a three-dimensional conformation isomeric to the three-dimensional structure of PrPC. This latter class of compositions of the invention is useful in research related aspects, such as, for example, production of antibody specific to PrPI.

The preparation of compositions is well known in the art. All such techniques known by one of skill in the art are appropriate for use in preparing the compositions of the present invention and are incorporated herein by reference. Additionally, the administration of the compositions of the present invention to a patient may be by any method known in the art. Thus, administration of the present invention to a recipient may be by a route selected from oral, parenteral (including, subcutaneous, intradermal, intramuscular, and intravenous) and rectal. For increased efficacy, the compositions of the present invention may be administered via localized delivery to the targeted tissue.

The compositions useful in the methods of the present invention further comprise a pharmaceutically acceptable carrier/vehicle. Pharmaceutically acceptable carriers/vehicles are known in the art and include aqueous solutions, non-toxic excipients, including salts, preservatives, buffers and the like, propylene glycol, polyethylene glycol, vegetable oil, injectable organic esters such as ethyloleate, water, saline solutions, parenteral vehicles such as sodium chloride and Ringer's dextrose, glycerol, lipids, alcohols.

Compositions of the present invention may be in any form known in the art, such as an orally digestible form, a sterile injectable form, forms suitable for delayed release, and forms that are enterically coated. Compositions of the invention may be in solid forms, including, for example, powders, tablets, pills, granules, capsules, sachets and suppositories, or may be in liquid forms including solutions, suspensions, gels and emulsions.

Preparation of antibodies is well known in the art. The use of any technique known by one of skill in the art for producing and preparing a PrPI antibody may be used herein, such as, for example, those described in Maniatis T. et al., "Molecular Cloning, a Laboratory Manual", Cold Spring Harbor Laboratory, Cold Spring Harbor, N.Y., 1982; Harlow, E. and Lane, D. (1988) *Antibodies: a Laboratory Manual*, Cold Spring Harbor Laboratory Press, Cold Spring Harbor, N.Y.; and Ausubel F. M. et al. (eds); "Current Protocols in Molecular Biology", John Wiley & Sons, New York, (1987) are incorporated herein by reference. Antibodies specific for the PrPI peptides of the invention preferably bind with high immunospecificity to PrPI protein, fragments, and peptides, recognizing PrPI epitopes that are not common to other proteins. The antibody of the invention may be polyclonal, monoclonal, fragments of monoclonal antibody, and/or recombinant antibody.

As is known by one of skill in the art, for monoclonal antibody technology hybridomas are produced using spleen cells from mice immunized with a particular prion protein of the invention. The spleen cells of each immunized mouse is fused with mouse myeloma cells, for example using the polyethylene glycol fusion method of Galfre, G. and Milstein, C., Methods Enzymol., 73:3–46 (1981). Growth of hybridomas, selection in HAT medium, cloning and screening of clones against antigens are carried out using standard methodology (Galfre, G. and Milstein, C., Methods Enzymol., 73:3–46 (1981)).

HAT-selected clones are injected into mice to produce large quantities of MAb in ascites as described by Galfre, G. and Milstein, C., Methods Enzymol., 73:3–46 (1981), which can be purified using protein A column chromatography (BioRad, Hercules, Calif.). MAbs are selected on the basis of their (a) specificity for a particular prion peptide, (b) high binding affinity, (c) isotype, and (d) stability.

MAbs can be screened or tested for specificity using any of a variety of standard techniques, including Western Blotting (Koren, E. et al., Biochim. Biophys. Acta 876:91–100 (1986)) and enzyme-linked immunosorbent assay (ELISA) (Koren, E. et al., Biochim. Biophys. Acta 876:91–100 (1986)).

It may be desirable to produce and use functional fragments of an MAb for a particular application. The well-known basic structure of a typical IgG molecule is a symmetrical tetrameric Y-shaped molecule of approximately 150,000 to 200,000 daltons consisting of two identical light polypeptide chains (containing about 220 amino acids) and two identical heavy polypeptide chains (containing about 440 amino acids). Heavy chains are linked to one another through at least one disulfide bond. Each light chain is linked to a contiguous heavy chain by a disulfide linkage. An antigen-binding site or domain is located in each arm of the Y-shaped antibody molecule and is formed between the amino terminal regions of each pair of disulfide linked light and heavy chains. These amino terminal regions of the light and heavy chains consist of approximately their first 110 amino terminal amino acids and are known as the variable regions of the light and heavy chains. In addition, within the variable regions of the light and heavy chains there are hypervariable regions which contain stretches of amino acid sequences, known as complementarity determining regions (CDRs). CDRs are responsible for the antibody's specificity for one particular site on an antigen molecule called an epitope. Thus, the typical IgG molecule is divalent in that it can bind two antigen molecules because each antigen-binding site is able to bind the specific epitope of each antigen molecule. The carboxy terminal regions of light and heavy chains are similar or identical to those of other antibody molecules and are called constant regions. The amino acid sequence of the constant region of the heavy chains of a particular antibody defines what class of antibody it is, for example, IgG, IgD, IgE, IgA or IgM. Some classes of antibodies contain two or more identical antibodies associated with each other in multivalent antigen-binding arrangements.

Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(ab')$_2$ fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

Fab and F(ab')$_2$ fragments of MAbs that bind particular blood prion peptides can be used in place of whole MAbs in methods for detecting or quantifying such proteins. Because Fab and F(ab')$_2$ fragments are smaller than intact antibody molecules, more antigen-binding domains can be immobilized per unit area of a solid support than when whole antibody molecules are used. As explained below, rapid, easy and reliable assay systems can be made in which antibodies or antibody fragment that specifically bind a prion peptide are immobilized on solid phase materials.

Recombinant DNA methods have been developed which permit the production and selection of recombinant antibodies which are single chain antigen-binding polypeptides known as single chain Fv fragments (ScFvs or ScFv antibodies). ScFvs bind a specific epitope of interest and can be produced using any of a variety of recombinant bacterial phage-based methods, for example as described in Lowman, H. B. et al., Biochemistry, 30: 10832–10838 (1991); Clackson, T. et al., Nature, 352: 624–628 (1991); and Cwirla, S. E. et al., Proc. Natl. Acad. Sci. USA, 87: 6378–6382 (1990), incorporated herein by reference. These methods are usually based on producing genetically altered filamentous phage, such as recombinant M13 or fd phages, which display on the surface of the phage particle a recombinant fusion protein containing the antigen-binding ScFv antibody as the amino terminal region of the fusion protein and the minor phage coat protein g3p as the carboxy terminal region of the fusion protein. Such recombinant phages can be readily grown and isolated using well-known phage methods. Furthermore, the intact phage particles can usually be screened directly for the presence (display) of an antigen-binding ScFv on their surface without the necessity of isolating the ScFv away from the phage particle.

More recent developments in the recombinant antibody technology demonstrate possibilities for further improvements such as increased avidity of binding by polymerization of ScFvs into dimers and tetramers (Holliger, P. et al., Proc. Natl. Acad. Sci. USA, 90: 6444–6448 (1993); Mezes, P. Construction and Biodistribution Studies of Multivalent Single-Chain Antibodies, The Fourth Annual IBC International Conference on Antibody Engineering, December 1993, Coronado, Calif.; Ito, W. and Kurosawa, Y., J. Biol. Chem., 268: 20668–20675 (1993), incorporated herein by reference).

Still another embodiment of the invention is directed to a method for treating a patient. Generally the method comprises administering an effective dose of a composition to a patient, wherein the composition comprises an antibody having specific affinity to a PrPI structural isomer. The patient may be any organism capable of developing a neuro-degenerative disease. Preferably, the patient of the invention is a mammal. In a particularly preferred embodiment, the patient is a human.

The compositions and methods of the invention are useful in screening and/or treating a patient afflicted with a prion-associated disorder. Preferably the disease is a prion-associated neurological disease. The neuro-degenerative disease may be at least one of the group consisting of mad cow disease, scrapie in sheep, Creutzfledt-Jacob disease, Gerstmann-Straussler-Scheinker disease, familial insomnia, and kuru. The disease may be in any stage of development.

The compositions and methods of the present invention may be administered to a recipient/patient as a single dose unit, or may be administered in several dose units, for a period ranging from one day to several years. The dose schedule is dependent upon at least the severity of disease, as well as the mode of administration. The effective dose of the compositions of the present invention is further dependent upon the body weight (BW) of the recipient/patient and also upon the chosen composition. Generally the compositions of the present invention are administered orally or intravenously.

The present invention is also directed to any and all methods for screening a patient for a prion-associated disorder, wherein the method comprises detection of a prion peptide isomeric to a wild-type prion. Generally the disorder is a neuro-degenerative disorder.

The invention further includes any and all methods for treating a patient having a neuro-degenerative disorder, wherein the method comprises inhibition of a prion peptide wherein the prion peptide is isomeric to a wild-type prion.

All references cited herein, including research articles, all U.S. and foreign patents and patent applications, are specifically and entirely incorporated by reference.

EXAMPLES

The following examples are provided to illustrate the present invention. These examples are not intended to limit the scope of the claims of the present invention, and should not be so interpreted.

Materials/Reagents

The following is a listing of reagents utilized herein, and the sources thereof: the plasmid pRBI-PDI-T7 for expression of mPrP(23-231), kindly supplied by Dr. Rudi Glockshuber (ETH, Switzerland); tryptone and yeast extract were purchased from Fisher Scientific; Isopropyl-b-D-thiogalactopyranoside (IPTG), 1,4-dithio-DL-threitol (DTT), phenylmethylsulfonyl fluoride (PMSF) and a-chymotrypsin were purchased from Sigma; Proteinase K was purchased from Boehringer Mannheim (Germany); Amicon Ultrafiltration unit and YM10 membranes were purchased from Millipore; Sephadex Fast-Flow and NAP-5 columns were purchased from Pharmacia; all chemicals were of analysis grade. Protein samples utilized for refolding analysis were further purified by reversed phase HPLC.

Example 1

Expression and Purification of Recombinant Mouse PrP(23-231)

Expression and purification of recombinant mPrp (23–231) was achieved using the method developed by Hornemann et al. (S. Hornemann et al., (1997) FEBS Lett. 413, 277–281.). Protein concentrations were measured by the Bradford method (purchased from Bio-Rad). The resulting purified proteins were verified by Edman Sequencing, matrix-assisted laser-desorption/ionization mass spectrometry with a time of flight detector (MALDI-TOF MS), SDS-PAGE and circular dichroism (CD).

Example 2

Oxidative Folding of mPrP(23-231)

The native mPrP(23-231) protein was first reduced and denatured by incubation in Tris-HCl buffer (0.1 M, pH 8.0) containing 100 mM of dithiothreitol and GdmCl (6M) at 23° C. for 90 minutes. The reducing reagent and denaturant were removed by passing the solution through a NAP-5 column (Pharmacia, G-25) equilibrated in 20 mM sodium acetate buffer (pH 5.0). Samples were then made ready for folding experiments by concentrating the protein to 2 mg/ml using Ultrafree centrifugal filters (Millipore, Biomax, 5K). In order to initiate protein folding, freshly prepared reduced/denatured protein was diluted to 0.2 mg/ml in buffers comprising a selected pH and concentration of urea.

Folding reactions were carried out at 23° C. in sodium acetate buffer (20 mM). The pH of the folding reaction was pH 4.0, as shown in FIG. 1, or was in the range of 2–9, as shown in FIG. 2. Folding intermediates were trapped in a time course manner by mixing aliquots of the sample with an equal volume of 4% aqueous trifluoroacetic acid at the time points indicated in FIG. 1. Samples were analyzed by HPLC using the following conditions: solvent A=water containing 0.088% trifluoroacetic acid; solvent B=90% acetonitrile in water (by volume) containing 0.084% trifluoroacetic acid; gradient=28–48% solvent B in 25 minutes; column=Zorbax 300 SB-C18 4.6 mm 25 cm, flow rate of=0.5 ml/min.; temperature of the column was 23° C.

In FIG. 1, N indicates the native mPrP(23-231) and R indicates the reduced mPrP(23-231). N and R were eluted at 17.8 min. and 22 min., respectively. Also in FIG. 1, a, b and c denote three novel isomers of the invention.

Example 3

Identification of Conformational Isomers of mPrP (23-231)

Prion isomers purified by HPLC were freeze-dried and modified with 4-vinylpyridine in a Tris-HCl buffer (pH 8.0) for 30 minutes at 23° C. Modified samples were desalted by a NAP-5 column using 0.5% TFA or by HPLC using the same conditions as stated above. All of the samples were analyzed by MALDI-TOF (matrix-assisted laser-desorption/ionization mass spectrometry with a time of flight detector) mass spectrometry.

Identification and Isolation of mPrP-a, mPrP-b and mPrP-c, Novel Species of Mouse Prion Protein.

These studies were conducted by examining the cumulative effects of six different pHs (3.0, 4.0, 5.0, 6.0, 7.0 and 8.0) and six different concentrations of urea (0M, 1M, 2M, 4M, 6M and 8M). The optimal pH for the preparation of the mPrP-a, mPrP-b and mPrP-c isomers was found to be 4.0 and the result is illustrated in FIG. 1. In buffer alone, reduced mPrP(23-231) (mPrP-R) folds directly to form native (oxidized) species (mPrP-N), albeit with a slow rate constant. Approximately 56% of the native mPrP(23-231) was recovered after 48 hours. When folding was performed at pH 4.0 in the presence of urea, mPrP-R was unable to form the native structure, and instead converted to three distinct species (mPrP-a, mPrP-b and mPrP-c) (FIG. 1). Their relative recovery depends on the time of folding and the concentration of urea. Prolonged folding in the presence of high concentrations of urea (6–8M) generates one predominant species (mPrP-a) with a purity of greater than 94%. The results from using a pH of 5.0 are similar to those obtained with a pH 4.0.

As the pH is increased to 6.0, the folding behavior of the reduced mPrP-R exhibits a dramatic change. Under these conditions, mPrP-a, mPrP-b and mPrP-c appear as transient intermediates, and mPrP-R is able to fold to from mPrP-N quantitatively during extended incubation at high concentrations (4–8M) of urea (FIG. 2). Similar results were obtained at pH 7.0. At pH 8, only negligible amounts of mPrP-a, mPrP-b and mPrP-c were observed and the folding proceeds directly from mPrP-R to mPrP-N (FIG. 2).

Surprisingly, mPrP-a, mPrP-b and mPrP-c were not detected in the presence of GdmCl. When mPrP-R was allowed to refold in buffer at pH 4.0 containing GdmCl (2M or 4M), more than 95% of the protein remained as starting material (mPrP-R) after 24 hours incubation. mPrP-R was also stable at pH 2.0 regardless of the concentration of urea.

mPrP-a, mPrP-b and mPrP-c Exist in Reduced State and Monomeric Form mPrP-a, mPrP-b and mPrP-c were separated by reversed phase HPLC and isolated in an HPLC solution consisting of about 60% of water, 40% acetonitrile and 0.1% of trifluoroacetic acid. The isomers are completely stable in lyophilized form when stored at −20° C. for up to 60 days. This was verified by HPLC analysis of lyophilized samples after reconstitution in the same HPLC solution used for their isolation (data not shown).

All three species, mPrP-a, mPrP-b and mPrP-c, each contain two free cysteines and exist in a reduced state. This evaluation is based on the molecular weight of the species modified with vinylpyridine (a cysteine specific reagent) and measured by MALDI-TOF mass spectrometry. The data are summarized in Table 1. Modification with vinylpyridine increases the molecular weight of mPrP-R, mPrP-a, mPrP-b and mPrP-c by 210 Dalton from 23,110 to 23,320, accounted for by two moles of conjugated vinylpyridine (M.W. 105). The molecular mass of the native species remains unchanged after modification with vinylpyridine (Table 1).

TABLE 1

Molecular Weight of prion isomers measured by mass spectrometry and light scattering

| Species | Expected | MALDI before[a] | MALDI after[b] | LS in HPLC solution (kDa)[c] | LS at pH 2.0 (kDa)[d] | LS at pH 5.0 (kDa)[e] |
|---|---|---|---|---|---|---|
| mPrP-N | 23107.4 | 23105.9 | 23106.7 | 23.3 ± 0.5 | 28.0 ± 0.4 | 22.3 ± 0.9 |
| mPrP-a | 23109.4 | 23107.8 | 23319.5 | 23.2 ± 0.2 | 28.3 ± 2.1 | 288.0 ± 13.6 |
| mPrP-b | 23109.4 | 23107.2 | 2331907 | 27.5 ± 0.2 | 25.8 ± 0.6 | 290.0 ± 4.2 |
| mPrP-c | 23109.4 | 23108.1 | 23320.1 | 27.6 ± 0.3 | 24.7 ± 0.5 | 220.0 ± 13.6 |
| mPrp-R | 23109.4 | 23107.9 | 23320.7 | 28.5 ± 0.3 | 28.2 ± 0.7 | 211.0 ± 3.2 |

[a]Determined by MALDI before modification with vinylpyridine.
[b]Determined by MALDI after modification with vinylpyridine.
[c]Measured by right angle light scattering in the HPLC solution consisting of 60% of water, 40% of acetonitrile and 0.1% of trifluoroacetic acid.
[d]Measured by right angle light scattering in the aqueous acidic solution containing 0.2% of trifluoroacetic acid (pH 2.0).
[e]Measured by right angle light scattering in the sodium acetate buffer (20 mM, pH 5.0).

Figure 6:
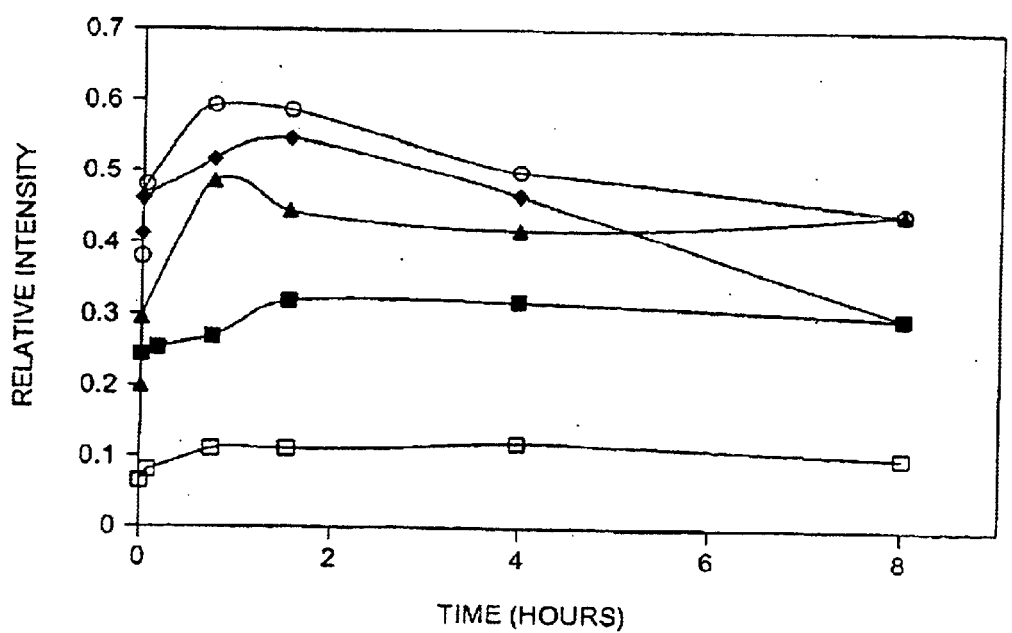
FIG. 6 depicts the results of right angle light scattering experiments performed on prion isomers a, b, and c.
Figure 12A:
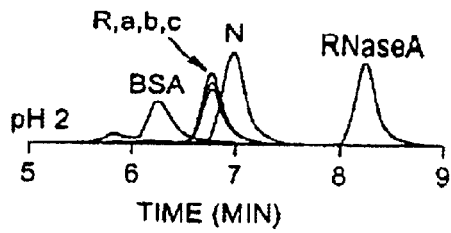
FIG. 12A shows the size-exclusion chromatography profiles of the native (n), and four reduced isoforms (R, a, b, and c) of mPrP(23-231)
Figure 12C:
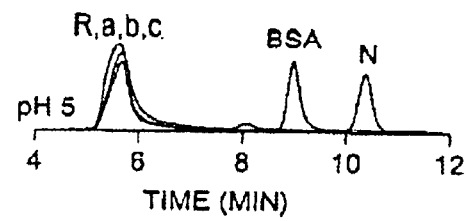
FIG. 12B shows the characterization of mPrP-Z and mPrP-N by size-exclusion chromatography (SEC). (Top panel 12A and 12B) Samples were eluted with 40% acetonitrile in water containing 0.1% trifluoroacetic acid (pH 2). (Bottom panel 12A 12B) Samples were eluted with 20 mM sodium acetate (pH 5.0 or 4.0) containing 200 mM NaCl. The column was TSK-GEL G3000 SWXL (30 cm×7.8 mm). Flow rate was 1.0 ml/min. Bovine serum albumin (BSA) (66,000) and ribonuclease A (RNase A) (14,000) were used as standards.

Since mPrP-R, both human (Cohen, F. E. and Prusiner S. B. (1998) *Annu. Rev. Biochem.* 67, 793–819; Maiti N. R. and Surewicz, W. K. (2001) *J. Biol. Chem.* 276, 2427–2431) and murine (Lu, B.-Y., Beck P. J. and Chang J.-Y. (2001) *Eur. J. Biochem.* 40, 13390–13396.), is known to form aggregates, the possibility was raised that mPrP-a, mPrP-b and mPrP-c may simply represent oligomeric species of mPrP-R. To clarify this question, molecular mass of the three novel species together with mPrP-R and mPrP-N were analyzed by size-exclusion chromatography (FIG. 12A) as well as right angle light scattering using a Triple Detector Array Model TDA 310 (Viscotek) (data provided in Table 1 and FIG. 6). Measurements by these two different techniques were conducted in three different solutions: (1) in the acidic HPLC solution (water/acetonitrile, 60/40 by volume, containing 0.1% trifuoroacetic acid) used for isolation of mPrP-a, mPrP-b, and mPrP-c; (2) in the acidic aqueous solution containing 0.2% trifluoroacetic acid (pH 2.0); and (3) in the acetate buffer of pH 5.0 (20 mM). In the first two acidic solutions, all species display molecular weight within the limit of 23,000 to 28,000, indicating that the vast majority of prion species exist in monomeric state (Table 1 and FIG. 12A). At pH 5.0, mPrP-N remains as a monomer. However, mPrP-a, mPrP-b and mPrP-c and mPrP-R rapidly form aggregates, with measured molecular mass ranging from 210,000 to 280,000 Dalton (corresponding to decamer) (Table 1)(FIG. 12A).

Not intending to be limited or bound by theory, the inventors believe that a plausible interpretation of these results is that mPrP-a, mPrP-b and mPrP-c differ from mPrP-R by their distinctive conformation rather than the state of oligomerization or the consequence of covalent modification. The results also demonstrate that reduced forms of prion protein are capable of adopting diverse conformations that are segregated by energy barrier and are stable in the acidic solution.

Figure 4:
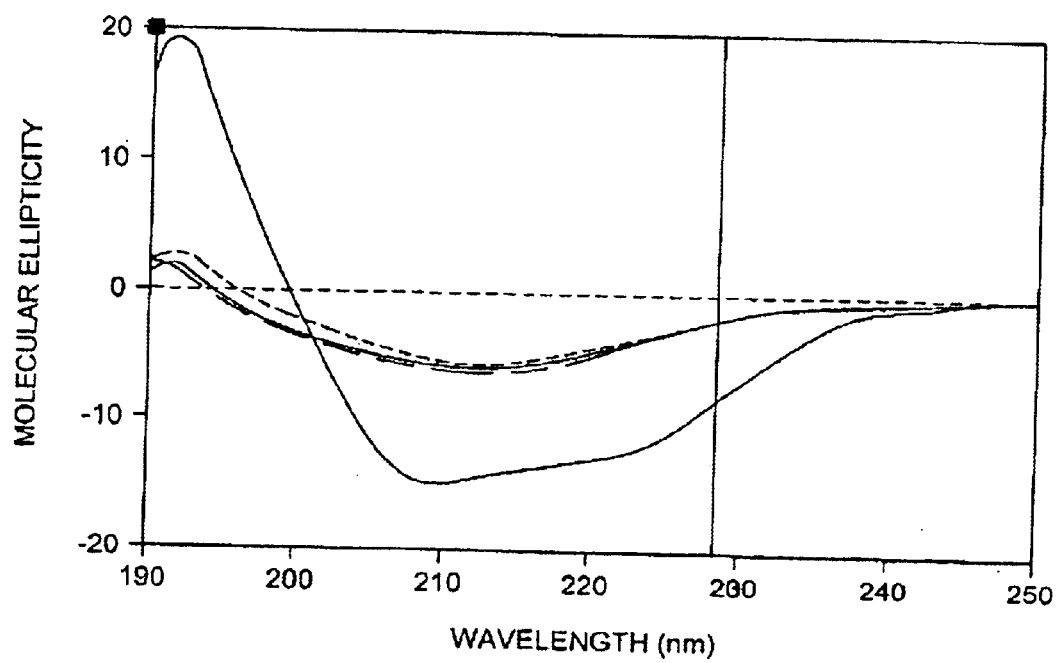
FIGS. 4A, 4B and 4C depicts far-UV circular dichroism spectra of conformational prion isomers a, b, and c wherein the solid line represents the spectrum of mPrP-N and the dashed and broken lines are spectra of mPrP-R, mPrP-a, mPrP-b, and mPrP-c, and wherein the solution used in 4B is an aqueous solution containing 0.2% trifluoroacetic acid (pH 2.0), and in 4A and 4C sodium acetate buffer (20 mM, pH 5.0).

Aggregates of mPrP-a, mPrP-b and mPrP-c Exhibit β-Sheet Structure and Resistance to Proteolysis The far-UV CD spectra of mPrP-a, mPrP-b, mPrP-c, mPrP-R and mPrP-N were measured both in the acidic solution (0.2% trifluoroacetic acid, pH 2.0) and in the sodium acetate buffer (20 mM, pH 5.0). Under both conditions, mPrP-N remains a monomer (Table 1) and exhibits a double minimum at 208 and 222 nm, characteristics for α-helical rich proteins (R. W. Woody (1995) Methods Enzymol. 246, 34–71) and consistent with those observed earlier (R. Riek et al., (1996) Nature 382, 180–182; D. G. Donne, et al., (1997) PNAS, USA 94,3452–3457; S. Hornemann et al., (1997) FEBS Lett. 413,277–281.) (FIGS. 4A, 4B and 4C). On the other hand, CD spectra of mPrP-a, mPrP-b, mPrP-c and mPrP-R differ significantly from that of mPrP-N and are determined by the state of their oligomerization. In monomeric state (pH 2.0), all four reduced isoforms exhibit coil structure with only a single strong dichroic band at about 200 nm. In oligomeric form at pH 5.0, all reduced isoforms display a single minimum at ~216 nm, a unique CD signal for proteins rich in β-sheet structure. These results (FIG. 12A and FIGS. 4A, 4B and 4C) clearly show that oligomerization of mPrP-a, mPrP-b, mPrP-c and mPrP-R is accompanied by a conformational change from random coil to predominant β-sheet structure.

mPrP-a, mPrP-b, mPrP-c and mPrP-R are also distinguished from the mPrP-N by their marked resistance to proteolysis. Susceptibility to limited proteolysis was assayed using both α-chymotrypsin (5B) and proteinase K (5A). In both cases, the four reduced isomers were shown to be more resistant than the mPrP-N (FIGS. 5A and 5B). When digestions were carried out for 1 h at 37° C. with 0.001% (by weight) of proteinase K, all reduced forms of isomers remained practically intact, while about 35% of the native mPrP(23-231) became fragmented under the same conditions. Resistance against proteolysis is likely to be a consequence of oligomerization of reduced prion protein under the selected experimental conditions. Alternatively, these results may also imply that the four reduced isomers are more stable than the native prion protein.

Reduced Form of Prion Isomers Display $PrP^{SC}$-like Structural Properties

The prion disease is caused by the conversion of cellular prion protein ($PrP^C$) to the infectious $PrP^{SC}$. According to the "protein-only" model, $PrP^{SC}$ differs from $PrP^C$ by conformation, acts as template for $PrPC \rightarrow PrP^{SC}$ transformation and propagation, and exists as diverse strains-associated isomers. To elucidate the underlying mechanism of prion disease will thus demand identification and isolation of stable conformational isomers of prion protein that exhibit $PrP^{SC}$-like structural properties.

The present study demonstrates that such stable prion isomers do exist. Three novel conformational isoforms of mouse prion protein were produced by incubating mPrP-R in the mild acidic solution containing urea. mPrP-a, mPrP-b and mPrP-c are each distinguished from $PrP^C$(mPrP-N) by a higher content of β sheet structure (FIG. 12A), a higher tendency to form aggregates (Table 1) and to resist proteolytic digestion (FIGS. 5A and 5B). These structural properties are characteristics of infectious PrP$^{SC}$. These data clearly demonstrate that mPrP-a, mPrP-b and mPrP-c, together with the reduced mPrP-R all possess PrP$^{SC}$-like structures.

Example 4

Polymerization of Mouse Prion Protein at Acidic pH in the Presence of Denaturant Freeze-dried native mPrP(23-231) (mPrP-N) (1 mg/ml) was dissolved in buffers of selected pH (2.0–6.0) and different concentrations of urea (2M to 6M) and GdmCl (0.5M to 4M). The reactions were performed at 23° C. The intermediates were trapped in a time course manner by removing aliquots of the sample and mixing with double volumes of 4% trifluoroacetic acid. Acid trapped samples were analyzed by HPLC using the following conditions. For the reversed phase HPLC: Solvent A was water containing 0.088% trifluoroacetic acid. Solvent B was 90% acetonitrile in water (by volume) containing 0.084% trifluoroacetic acid. The gradient was 28–48% solvent B in 25 minutes. The column was ZORBAX 300 SB-C18 4.6 mm 25 cm. The flow rate was 0.5 ml/min. For size-exclusion chromatography: the column was TSK-GEL G3000 SWXL (30.0 cm×7.80 mm) equilibrated and eluted with either the sodium acetate buffer (20 mM, pH 4.0) containing 0.2M NaCl, or an aqueous solution containing 0.2% trifluoroacetic acid (pH ~2.0), or a 40% aqueous acetonitrile containing 0.1% trifluoroacetic acid (pH ~2.0).

Preparation and Isolation of mPrP-z, a Polymerized Mouse Prion Protein mPrP(23-231)

Figure 7A:
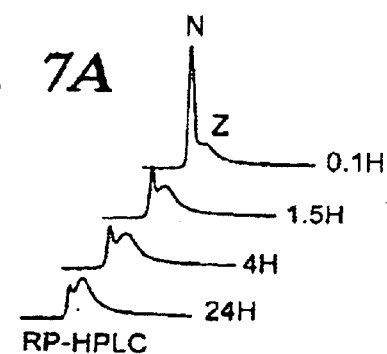
FIG. 7 depicts the reversed phase HPLC (RP-HPLC) and size exclusion chromatography (SEC) results from polymerization of native mPrP(23-231) at pH 4.0 in the presence of 2M GdmCl at 0.1, 1.5, 4.0 and 24.0 hours.
Figure 7B:
Figure 2A:
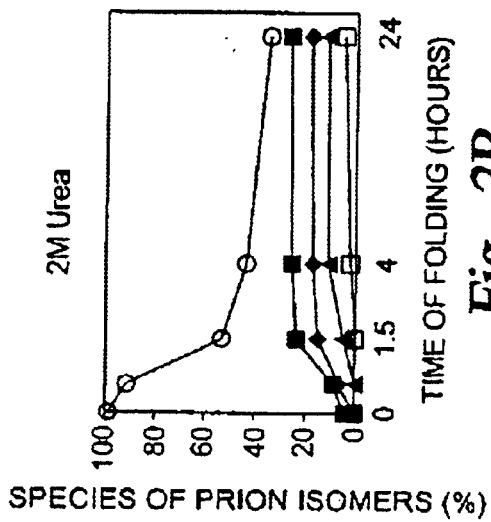
FIG. 2 depicts the effects of varying pH and urea concentration on the folding of mPrP(23-231) wherein the following five different species of prion isomers were recovered based on HPLC peak area integration: (□) mPrP-N; (○) mPrP-R; (▲) mPrP-a; (♦) mPrP-b; and (■) mPrP-c.
Figure 2B:
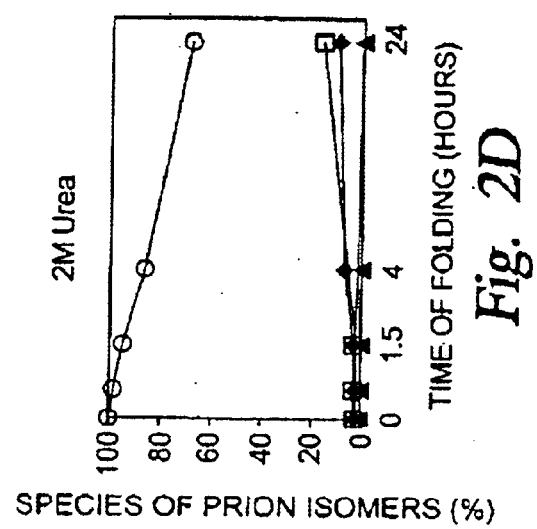
Figure 2C:
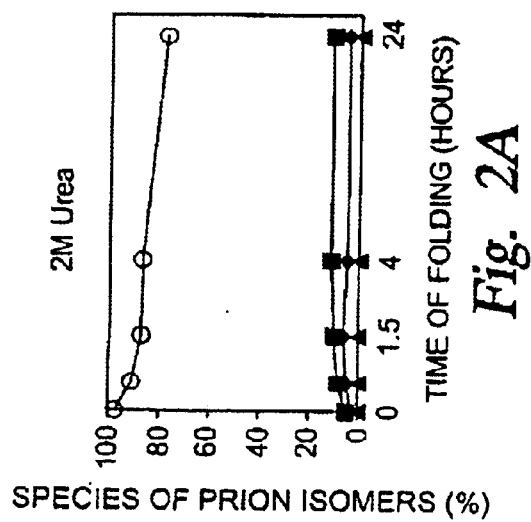
Figure 2D:
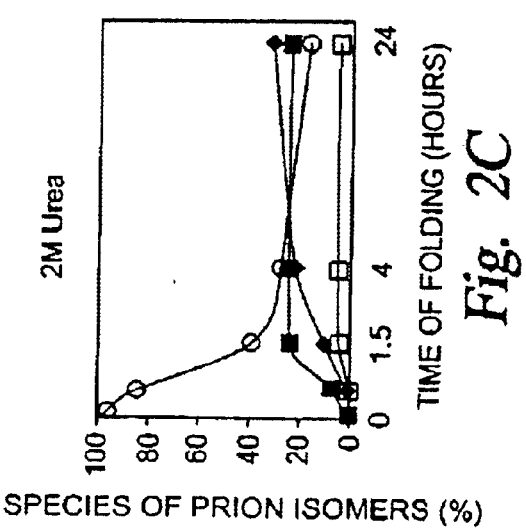
Figure 2J:
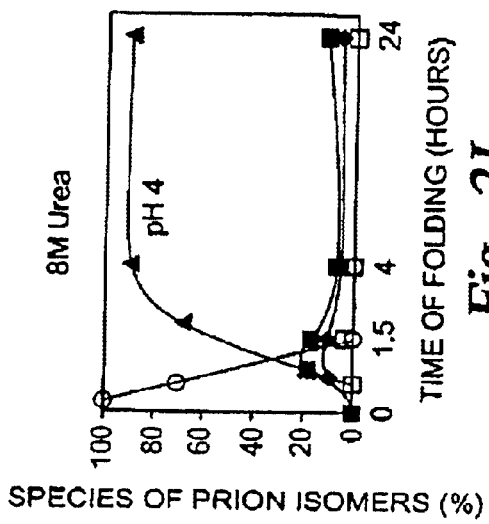
Figure 2L:
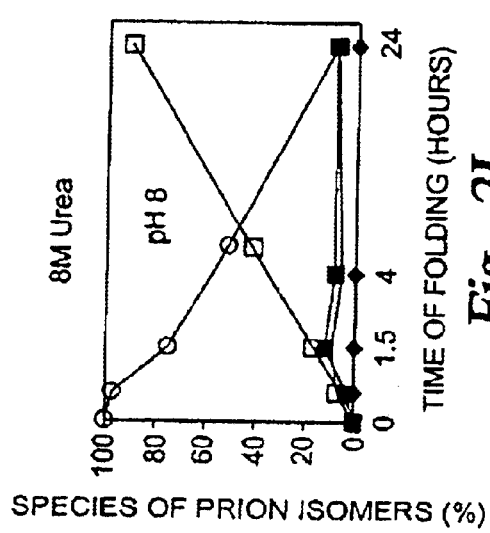
Figure 2I:
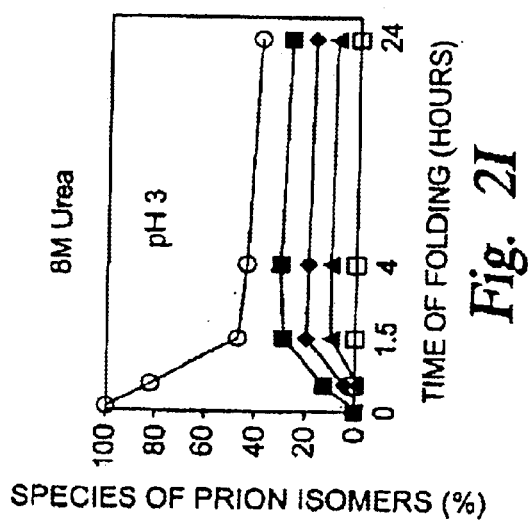
Figure 2K:
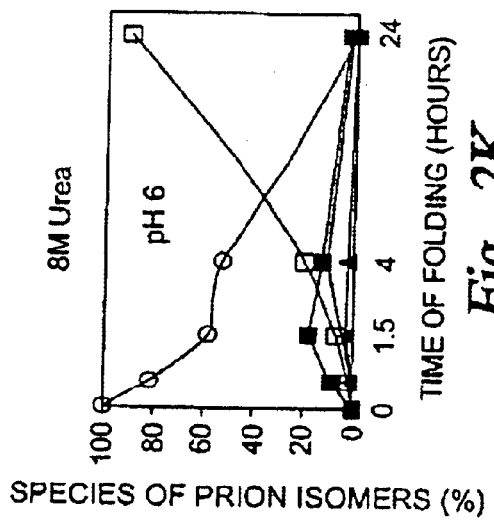

In the presence of mild concentration of denaturant and acidic pH, the native form of mouse prion protein mPrP(23-231) (mPrP-N) underwent a structural transformation leading to the process of polymerization. The reaction can be measured by determining the yield of polymerized product and followed by both reversed phase HPLC and size-exclusion chromatography (FIG. 7). One polymerized prion protein isomer, designated mPrP-z, was found to be stable under acidic conditions and can be isolated and purified for further structural analysis.

FIG. 7 shows chromatograms of the time-course conversion of mPrP-N to mPrP-Z at pH 4.0 in the presence of 2M GdmCl. Baseline separation of m-PrP-N and mPrP-z can be achieved by size-exclusion chromatography. Kinetic analysis of the formation of mPrP-z was thus primarily based upon data analyzed by size-exclusion chromatography.

Polymerization of m-PrP-N to form mPrP-z appears to occur under a wide range of conditions that include both acidic pH and denaturant. A first objective was to establish the optimized conditions for the production of mPrP-z. In order to achieve this aim, systematic studies were performed by examining the collective effects of utilizing varying pH (pH 2.0 to pH 6.0) and different concentrations of either urea (2M to 6M) or GdmCl (0.5M to 4M). The results, summarized in FIG. 8 and FIG. 9, lead to the conclusion that the most efficient conditions for the production of the mPrP-z isomer are the combination of either pH 4.0 and 2M GdmCl or pH 2.0 and 5M urea.

Figure 8A:
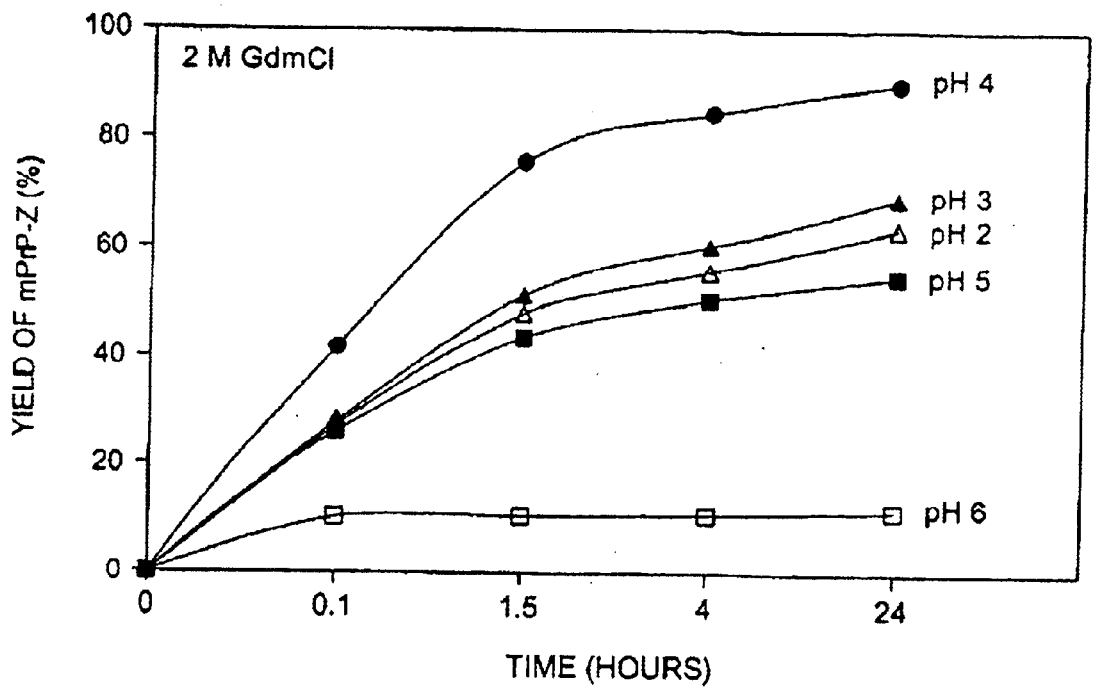
FIG. 8 shows the effects of varying pH on the kinetics of polymerization of mPrP-N to produce mPrP-Z at selected concentrations of denaturant.
Figure 8B:
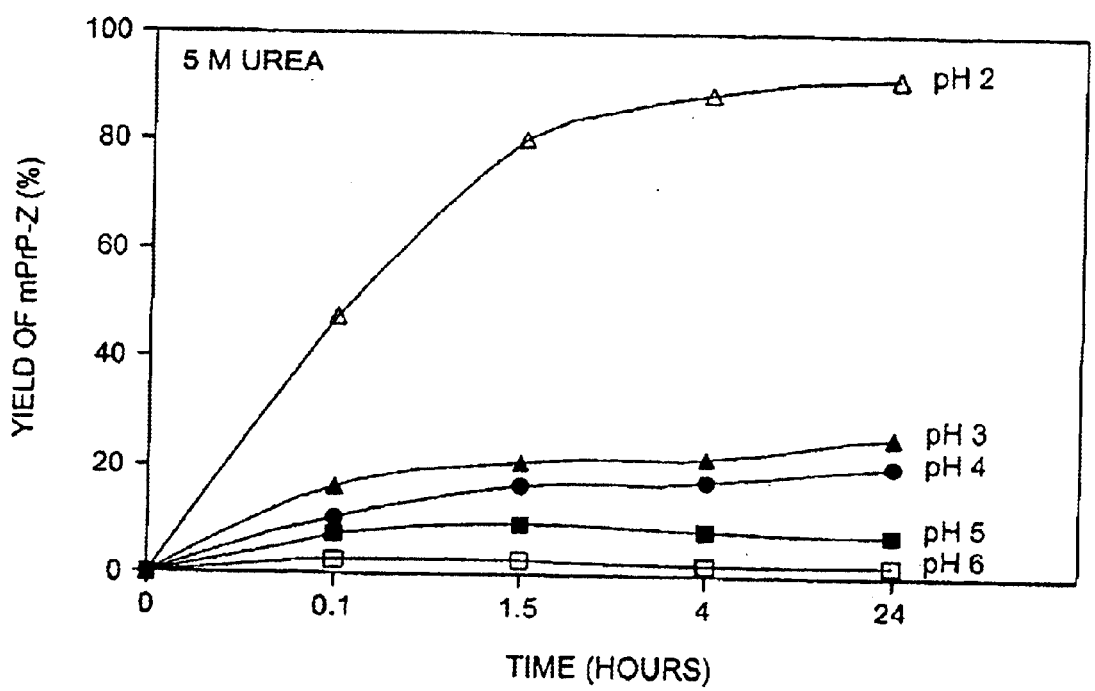
Figure 9A:
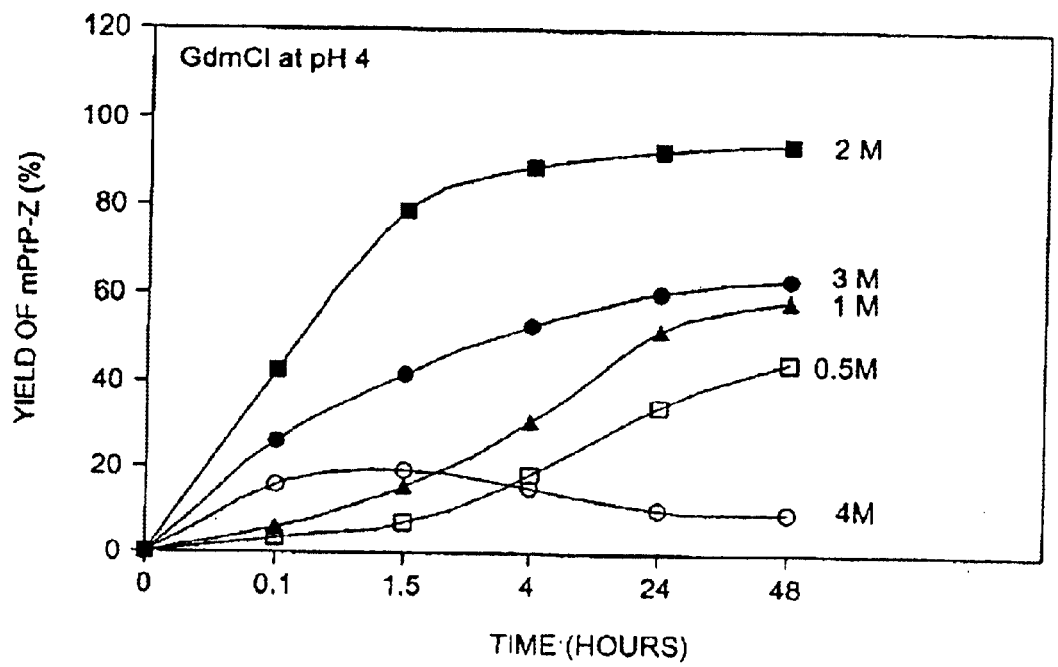
FIG. 9 shows the influence of concentration of denaturant on the kinetics of polymerization of mPrP-N at selected pH.
Figure 9B:
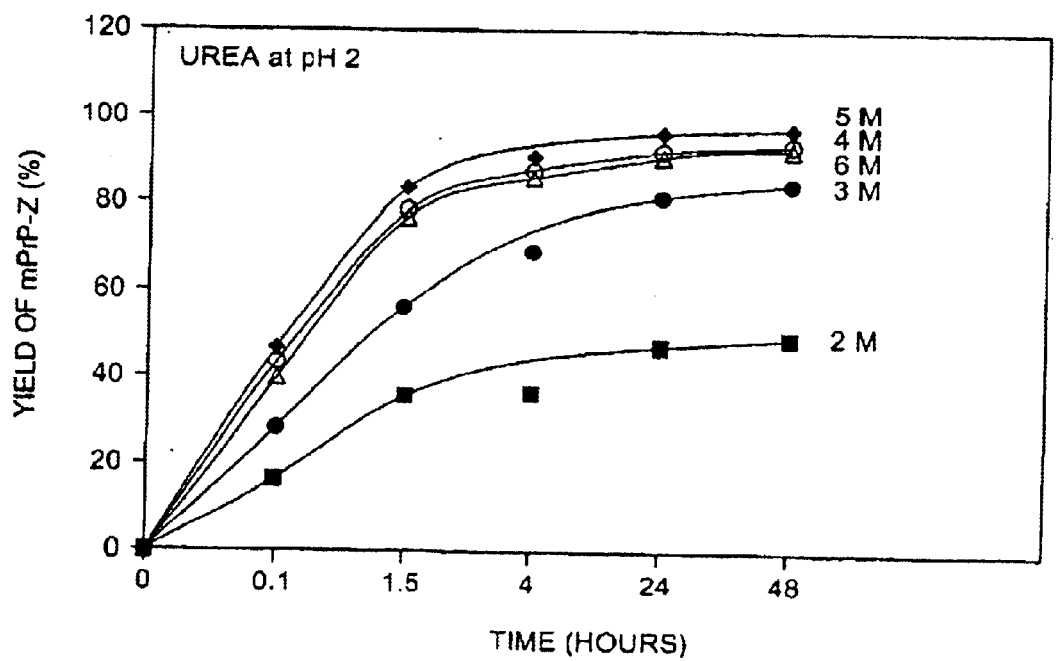

The effect of pH was found to be most significant for urea-induced polymerization. Low pH (2.0) is required for the near quantitative recovery of mPrP-z (FIG. 8, right panel). At 5M urea, pH increase from 2.0 to 3.0 reduced the yield of mPrP-z isomer by 70%. The concentration of urea is less crucial. High yield of mPrP-z isomer was similarly obtained at pH 2.0 in the presence of 4M and 6M urea (FIG. 9, right panel). It was also found that at pH 4.0, the optimized concentration of urea is 3.5 M. However, the yield of mPrP-z isomer is low in comparison to that obtained at pH 2.0 and 5M urea.

In the case of GdmCl-induced polymerization (i.e., isomerization buffer comprising GdmCl), the concentration of denaturant and the range of pH are about equally critical. At 2M GdmCl, about 90% of mPrP-z isomer was recovered within 4 hours when the reaction was carried out at pH 4.0. As the pH was increased from 4.0 to 6.0, the yield of mPrP-z decreased to less than 10% (FIG. 8, left panel). At optimized pH (4.0), adjustment of the concentration of GdmCl by one unit from 2M to either 1M or 3M decreased the yield of mPrP-z by nearly 40% (FIG. 9, left panel).

Figure 10:
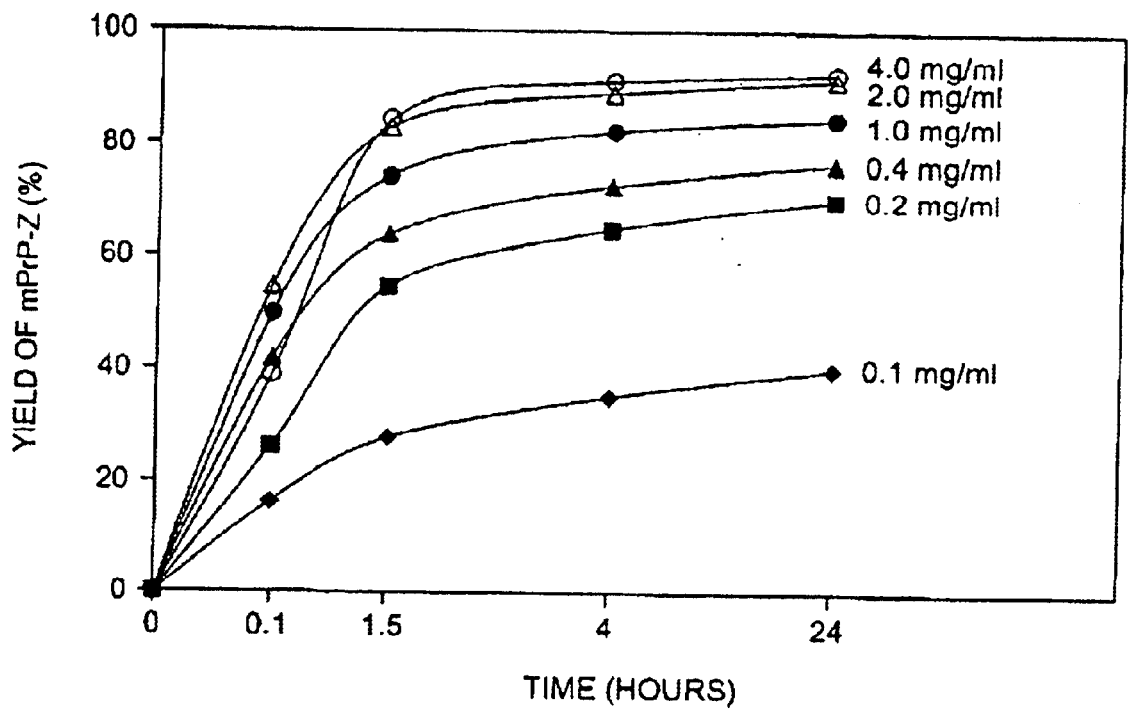
FIG. 10 shows the effects varying the concentration of mPrP-N has on the polymerization of mPrP-N.
Figure 11:
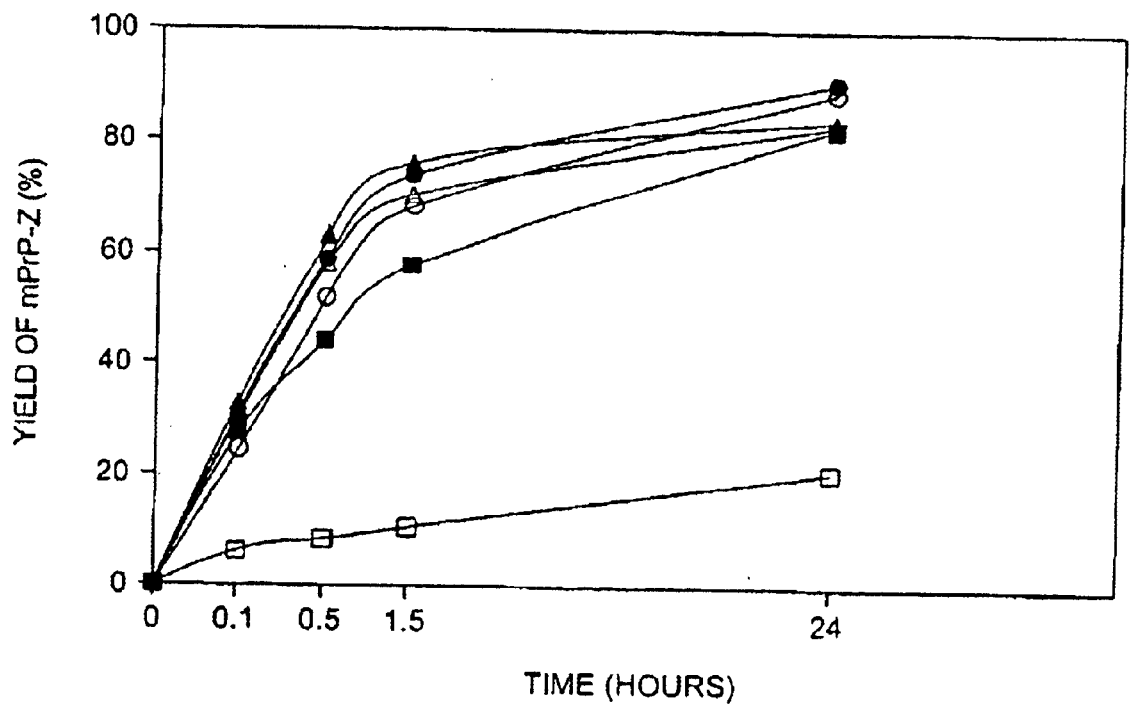
FIG. 11 shows the effect of salt (NaCl) on the production of mPrP-Z under the following conditions: 2M GdmCl, pH 4.0 (Δ); 2M GdmCl, pH 4.0, plus NaCl (▲); 5M urea, pH 2.0 (○); 5M urea, pH 2.0, plus NaCl (●); 3.5M urea, pH 4.0 (□); 3.5M urea, pH 4.0, plus NaCl (■).

Production of mPrP-z is also dependent upon protein concentration. The higher the protein concentration, the greater the yield of mPrP-z (FIG. 10). Under otherwise optimized conditions (pH 4.0 and 2M GdmCl), increasing the protein concentration from 0.1 mg/ml to 2.0 mg/ml improved the recovery of mPrP-z isomer from 40% to 92% after 24 hours of reaction. Although not intending to be limited by theory, this phenomenon is not surprising since high protein concentration is believed to facilitate intermolecular interactions and promote the polymerization of denatured mPrP-N. The influence of salt on the formation of mPrP-z was also investigated. The inclusion of NaCl (150 mM) resulted in no detectable effect on the recovery of mPrP-z isomer, when the reaction was performed at either pH 4.0 and 2M GdmCl or pH 2.0 and 5M urea. However, the presence of 150 mM NaCl increased the yield of mPrP-z isomer by about 4-fold when the reaction was carried out at 3.5M urea and pH 4.0 (FIG. 11).

Evidence that mPrP-z Exists in Oxidized State and Polymerized Form

Figure 12B:
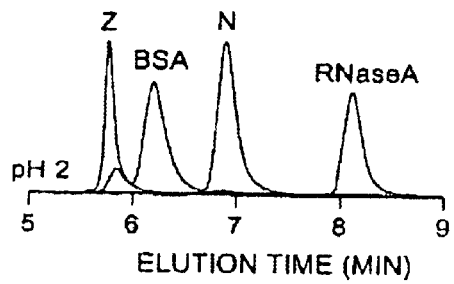
Figure 12D:
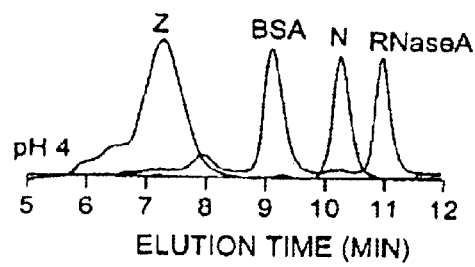

The molecular weight of mPrP-z was characterized by both size exclusion chromatography as well as right angle light scattering using a Triple Detector Array Model TDA 310 (Viscotek) (Table 2). In the acidic solution of pH 2.0 and pH 4.0, mPrP-z was eluted near the void volume of the TSK-GEL G3000 column and displays a molecular weight of greater than that of bovine serum albumin (66,000) (FIG. 12B). Analysis by light scattering at both pH 2.0 and 4.0 reveal the molecular mass of mPrP-z in the range of 315,000 to 355,000 Dalton (corresponding to greater than a decamer) (Table 2).

TABLE 2

Molecular weight of mPrP-z

| species | expected (Da) | Measured by MALDI Modified with VP without reduction | Measured by MALDI Modified with VP after reduction | Measured by RALS at pH 2 (kDa)[a] | Measured by RALS at pH 4 (kDa)[b] |
|---|---|---|---|---|---|
| mPrP-N | 23107.4 | 23107.4 | 23319.5 | 31.8 ± 1.6 | 23.5 ± 0.2 |
| mPrP-z | — | 23109.8 | 23322.5 | 353.8 ± 8.7 | 314.9 ± 3.7 |

[a]Measured by right angle light scattering in an acidic solution containing 60% water, 40% acetonitrile and 0.1% trifuloroacetic acid.
[b]Measured by right angle light scattering in 20 mM sodium acetate, pH 4.0.

Figure 13:
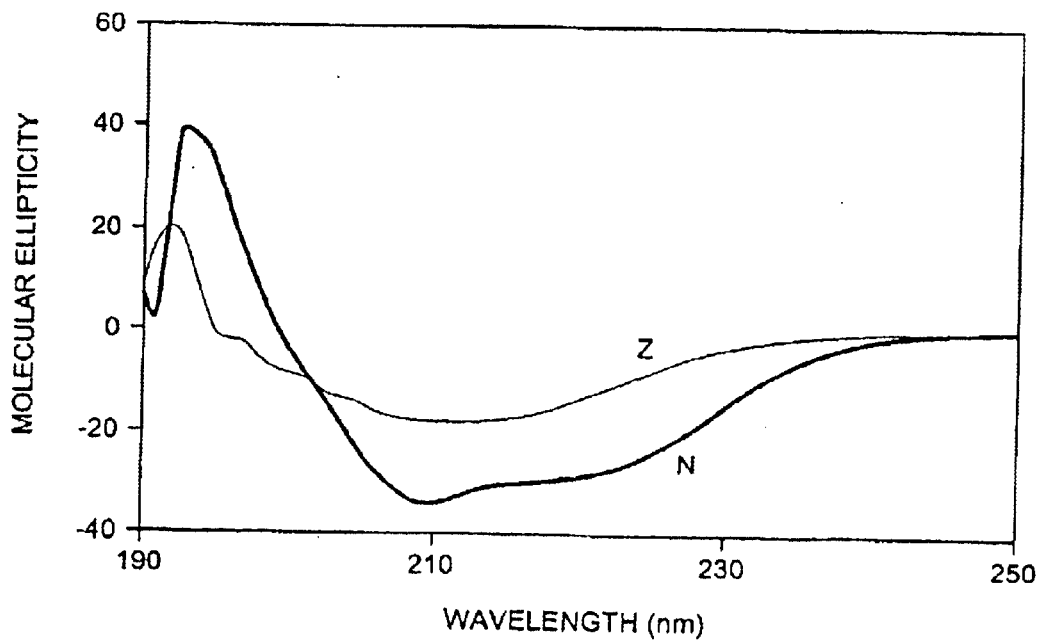
FIG. 13 shows the results of far-UV circular dichroism spectra analysis of mPrP-Z and mPrP-N.

The disulfide bond of prion protein remains intact in mPrP-z. This conclusion is based on the analysis of molecular weight of mPrP-z modified with vinylpyridine (a cysteine specific reagent) before and after reduction with dithiothreitol. The data are summarized in Table 2. It is important to note that during the analysis by MALDI mass spectrometry, polymerized mPrP-z apparently dissociates to form the monomeric form of prion protein. Without reduction, vinylpyridine-modified mPrP-z exhibits a molecular mass of 23,109, identical to that of mPrP-N. After reduction followed by vinylpyridine modification, the molecular mass of mPrP-z increases by 210 Dalton from 23,109 to 23,319, accounted for by two moles of conjugated vinylpyridine (M.W. 105). These data indicate that the two cysteines of mPrP-z are engaged in disulfide bonding and are not accessible to vinylpyridine modification.

mPrP-z Displays a High Content of β-Sheet Structure but Lacks Resistance to Proteolytic Digestion The far-UV CD spectra of mPrP-N and mPrP-z were measured in sodium acetate buffer (20 mM, pH 4.0) (results shown in FIG. 13). mPrP-N exhibits a double minimum at 208 and 222 nm, characteristics for α-helical rich proteins and consistent with those observed earlier (S. Hornemann, et. al. (1997) FEBS Lett. 413, 277–281; R. Riek, et. al., (1997) FEBS Lett. 413, 282–8; D. G. Donne, et al., (1997) PNAS 94, 3452–3457. The CD spectra of the mPrP-z isomer on the other hand, differs significantly from that of mPrP-N, and displays a single minimum at ~215 nm, a CD signal believed to be unique for proteins rich in β-sheet structure (S. Hornemann, et al., (1998) PNAS USA 95, 6010–6014; W. Swietnicki, et al., (1997) JBC 272, 27517–27520; G. S. Jackson et al., (1999) Science 283, 1935–1937; B. Y. Lu, and J.-Y. Chang, (2001) Biochemistry, 40, 13390–13396.

Figure 14:
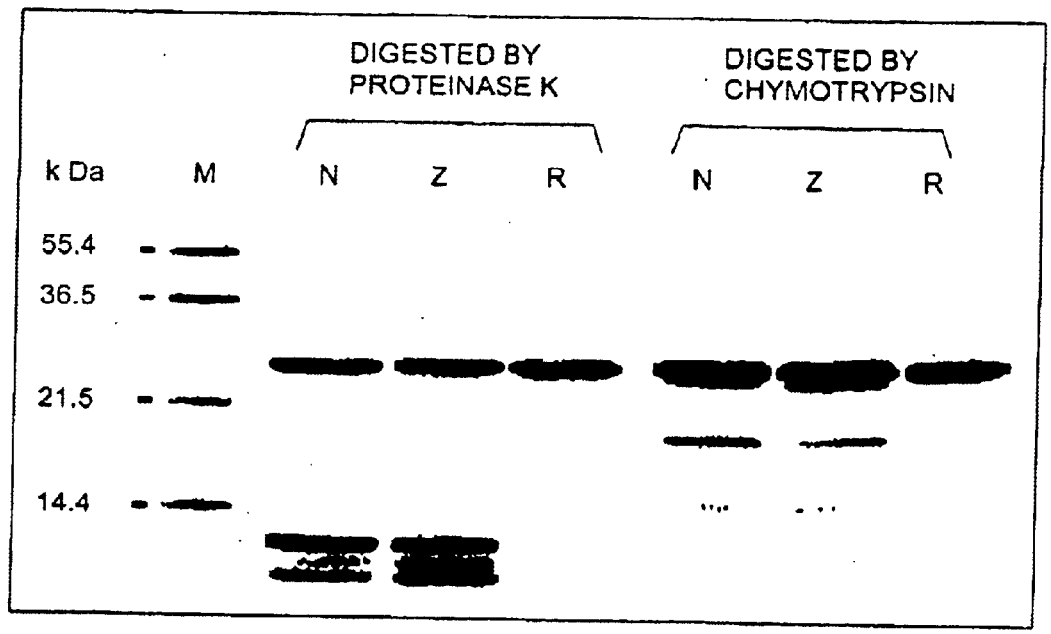
FIG. 14 provides the SDS-PAGE results of the proteolytic digestion of native (N=native) and isoforms ®=reduced, Z=polymerized) of mPrP(23-231) where N, Z, and R represent mPrP-N, mPrP-Z, and mPrP-R, respectively.
Figure 15A:
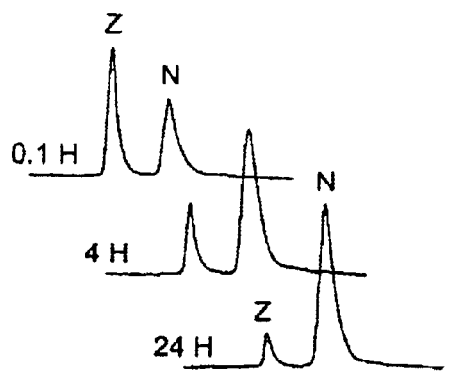
FIG. 15 depicts the results of depolymerization of mPrP-Z to form mPrP-N under basic conditions in the presence of denaturant. (Top panel) Size exclusion chromatography of the time course depolymerization of mPrP-Z in the presence of 6M GdmCl and 8M urea. (Bottom panel) Effects of the concentration of GdmCl and urea on the kinetics of depolymerization of mPrP-Z.
Figure 15B:
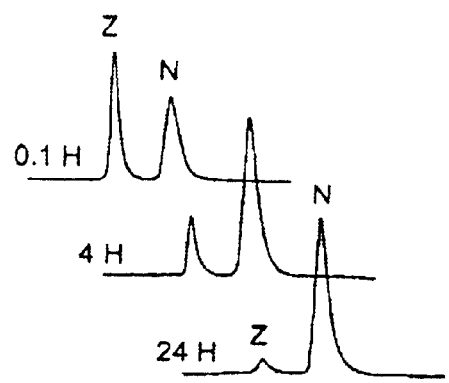
Figure 15C:
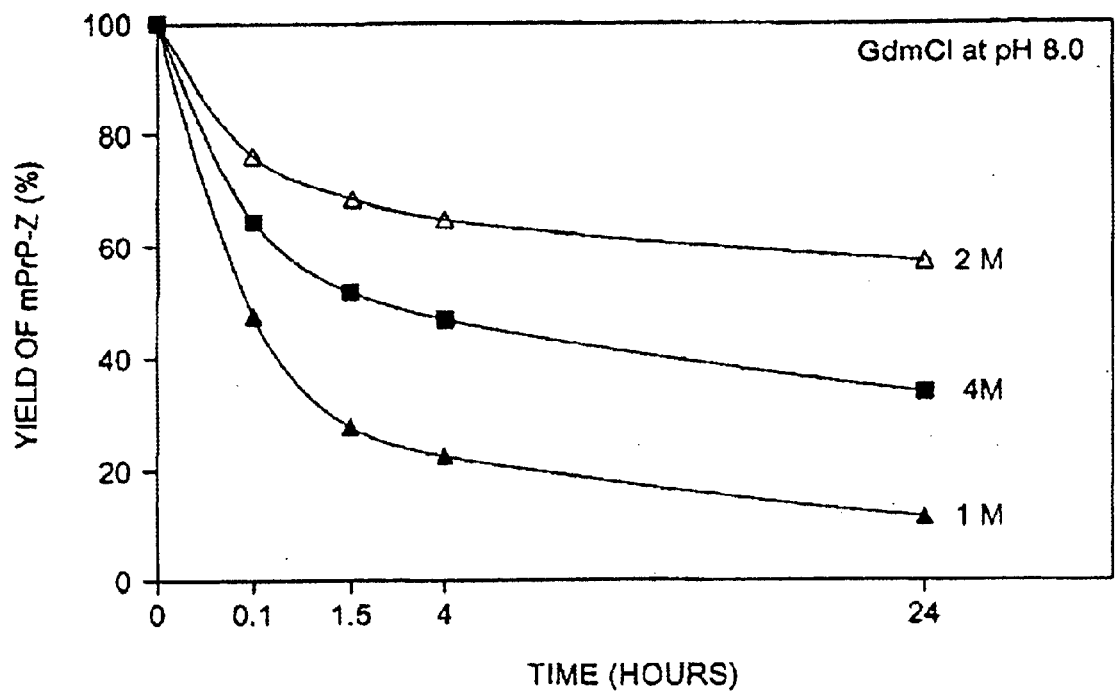
Figure 15D:
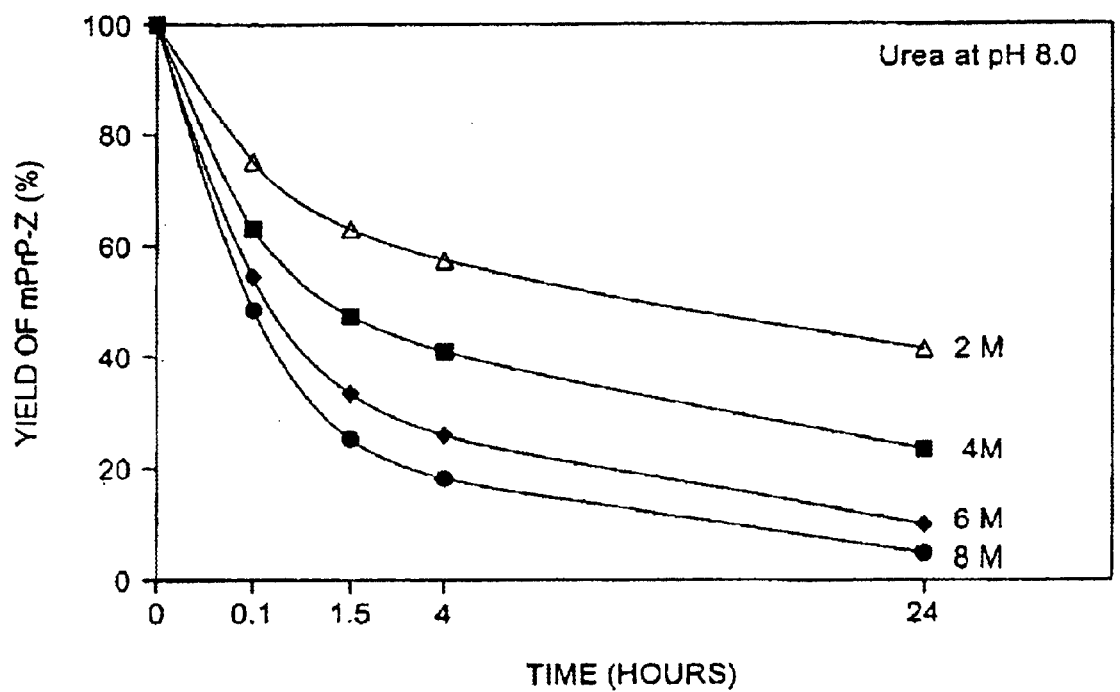

However, with respect to susceptibility to proteolysis, mPrP-z isomer is indistinguishable from mPrP-N. Susceptibility to limited proteolysis was analyzed using both α-chymotrypsin and proteinase K. In both cases, the m-PrP-N wild-type prion and the mPrP-z prion isomer were readily digested by the enzymes (FIG. 14). When digestions were carried out for 1 h at 37° C. with 0.001% (by weight) of proteinase K, about 55% of mPrP-N and 65% of mPrP-z were fragmented. The sensitivity of mPrP-z toward proteolysis contrasts sharply to that of the four isomers, mPrP-a, mPrP-b, mPrP-c, and mPrP-R, of reduced mouse prion protein (B. Y. Lu, P. J. Beck, and J.-Y. Chang (2001), *Eur. J. Biochem.* 268, 3767–3773; B. Y. Lu, and J.-Y. Chang, (2001) Biochemistry, in press). Under reaction conditions equivalent to those above, all four reduced mouse prion protein isomers mPrP-a, mPrP-b, mPrP-c, and mPrP-R were found to be almost totally resistant to proteolysis (compare FIG. 14 to FIG. 5). Results obtained from the digestion of mPrP-R are also presented in FIG. 14, right lane.

Example 5

Depolymerization of Polymerized Mouse Prion Protein

Polymerized mPrP-z isomer (freeze-dried) was incubated in buffers of either pH 4.0 (20 mM sodium acetate) or pH 8.0 (0.1M Tris-HCl) containing different concentrations of urea (2M to 8M) and GdmCl (2M to 6M). The reactions were performed at 23° C. The kinetics of depolymerization was monitored by removing aliquots of the sample at different time points and mixing with double volumes of 4% trifluoroacetic acid. Acid trapped samples were then analyzed by size-exclusion chromatography using the conditions described above in Example 4.

Briefly, mPrP-z was isolated by size-exclusion chromatography eluted with an acidic solution (pH 2.0) that consists of 60% of water, 40% of acetonitrile and 0.1% of trifluoroacetic acid. Isolated mPrP-z is completely stable in lyophilized form when stored at −20° C. for up to 60 days. This was verified by analysis of lyophilized samples after reconstitution in the same acidic solution (data not shown). mPrP-z also remains stable when incubated at pH 4 (50 mM sodium acetate) in the absence of denaturant for at least 48 hours without sample precipitation or depolymerization. As the pH was adjusted to 8.0 (100 mM Tris-HCl), mPrP-z rapidly formed insoluble aggregates and gradually precipitates out of the solution.

However, mPrP-z may depolymerize and convert back to mPrP-N in the alkaline buffer containing high concentrations of denaturant. Studies were conducted at pH 8.0 in the presence of varying concentrations of GdmCl and urea. The results shown in FIG. 15 clearly show that depolymerization of mPrP-z is promoted by the high concentration of denaturant. At pH 8.0, complete depolymerization may be achieved within 24 hours in the presence of 8M urea.

Example 6

Stop and Go Folding of Conformational Isomers of mPrP(23-231)

Figure 3:
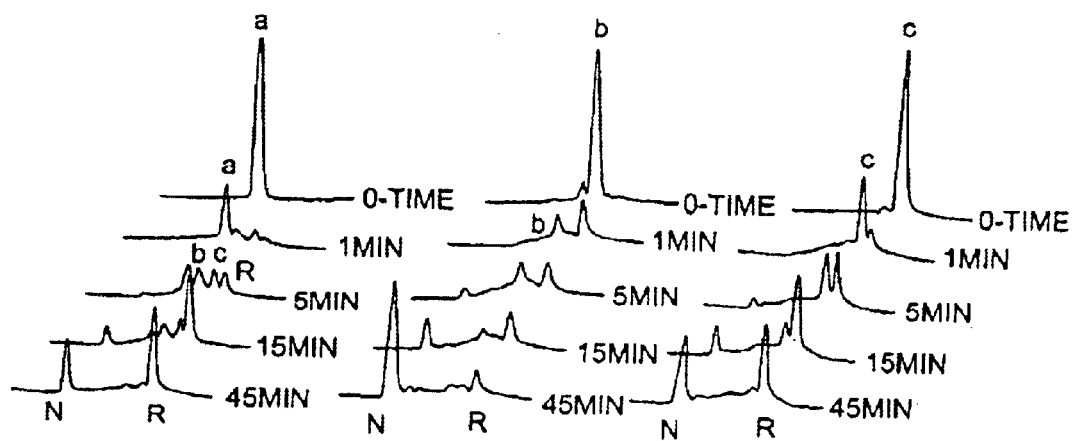
FIG. 3 depicts the HPLC analysis results following the stop/go folding of mPrP-N and mPrP-R, and the prior isomers mPrP-a, mPrP-b, and mPrP-c.

Purified prion isomers were freeze-dried and solubilized in acetate buffer (20 mM, pH 4.0) to a concentration of 2 mg/ml. To initiate folding, the samples were diluted to a final protein concentration of 0.2 mg/ml using Tris-HCl buffer (0.1 M, pH 8.0) containing 4.4 M urea. Folding reactions were performed at 23° C. in Tris-HCl buffer (0.1M, pH 8.0) containing 4M urea. Aliquots were trapped in a time course manner by mixing aliquots of the sample with an equal volume of 4% trifluroacetic acid (in water) as described in Example 2. Results are shown in FIG. 3.

While mPrP-a, mPrP-b and mPrP-c are stable as monomers in the acidic HPLC solution, they are apparently able to fold to form the native (oxidized) mPrP(23-231)(mPrP-N) after reconstitution in alkaline buffer containing urea. Their folding pathway(s), carried out in the Tris-HCl buffer (0.1 M, pH 8.0) containing 4M urea, are shown FIG. 6. mPrP-a, mPrP-b and mPrP-c isomers appeared to be incapable of converting directly to mPrP-N. Instead, all three must fold back to mPrP-R, which is then converted to the native structure.

For mPrP-a to reach the native structure, it used pathways either via mPrP-b or mPrP-c as intermediates; (1) mPrP-a→mPrP-b→mPrP-R→mPrP-N; or (2) mPrP-a→mPrP-c→mPrP-R→mPrP-N. In contrast to mPrP-a, both mPrP-b and mPrP-c directly fold back first to mPrP-R and then to mPrP-N. The assays also demonstrate that under identical conditions, mPrP-b more efficiently converts back to mPrP-R and subsequently to the native structure than do either mPrP-a or mPrP-c. It should be noted that mPrP-a, mPrP-b and mPrP-c are not oligomers of mPrP-R. Analysis by size exclusion chromatography (TSK Gel 3000SW) and light scattering demonstrates that mPrP-a, mPrP-b and mPrP-c each differ from mPrP-R by their distinctive conformation.

Not intending to be bound or limited by theory, the inventors believe that the most striking finding of this analysis is that these three isomers together with mPrP-R are partitioned by kinetic rather than thermodynamic control. Isomers mPrP-b and mPrP-c are apparently segregated by an energy barrier that is far greater than that between mPrP-b and mPrP-R, or between mPrP-c and mPrP-R. Kinetic partition of protein conformations is not a prevailing phenomenon in the field of protein folding, nonetheless, it has been demonstrated in numerous cases (J. F. Sinclair, et al., (1994) Nature Struct. Biol. 5, 320–326; C. R. Matthews, (1993) Ann. Rev. Biochem. 62, 653–683.) and has been predicted to be one of the unique properties of prion molecules (S. B. Prusiner, (1999) PNAS, USA 95, 13363–13383; F. E. Cohen, and S. B. Prusiner, (1998) Annu. Rev. Biochem. 67, 793–819.).

Example 7

Measurement of Circular Dichroism Spectrometry

Far-UV circular dichroism (CD) was recorded on a Jasco J-715 spectropolarimeter at 23° C. mPrP-a, mPrP-b and mPrP-c and PrP-N control samples were solubilized at a protein concentration of 0.2 mg/ml in sodium acetate buffer (20 mM, pH 5.0), and mPrP-z and PrP-N control samples were at a concentration of 0.5 mg/ml in 20 mM sodium acetate buffer (pH 4.0) in the presence of 2M GdmCl. The spectra were recorded in a 0.1 cm cuvette in the far-UV region (190–250 nm). In FIGS. 4A, 4B and 4C, the solid line represents the native mPrP(23-231), and dashed and broken lines represent spectra of mPrP-a, mPrP-b and mPrP-c, three isomers of the invention.

Example 8

Right Angle Light Scattering Experiments for Analysis of Protein Aggregation HPLC isolated prion isomers were freeze-dried and solubilized in acetate buffer (20 mM, pH 4.0) to 2 mg/ml. The samples were diluted 10-fold with Tris-HCl buffer (0.1 M, pH 8.0) to a final protein concentration of 0.2 mg/ml.

Average molecular weight of protein was measured by right angle light scattering method using a TDA Triple Detector Array (Viscotek, Houston Tex., USA). Lysozyme (Viscotek, MW 14307 Da) and bovine serum albumin were used as calibration standards. The triple detector array (light scattering, viscometry and refraction index) was connected to an Agilent 1100 HPLC isocratic pump system and an autosampler. The system was equilibrated with specified buffer at a flow rate of 1.0 ml/min. Samples were injected through autosampler directly into detector array. The molecular mass of prion protein was also measured by matrix-assisted laser-desorption/ionization mass spectrometry with a time of flight detector (MALDI-TOF MS, Voyager-DE™ STR, from PerSeptive Biosystems). Horse myoglobin (Sigma, MW 16,952 Da) and Carbonic anhydrase (Sigma, MW 29,022 Da) were used as calibration standards.

In FIGS. 4A, 4B and 4C, N represents the native mPrP (23-231), R represents the reduced mPrP(23-231), and a, b, and c represent three isomers of the invention, mPrP-a, mPrP-b, and mPrP-c, respectively.

Example 9

Figure 5:
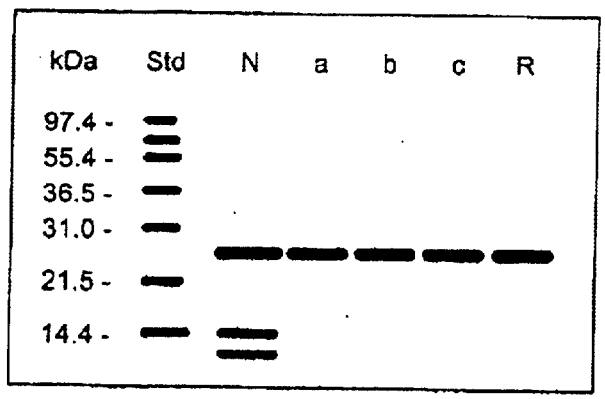
FIGS. 5A and 5B depict the results obtained following proteolytic digestion of mPrP-N (N), mPrP-a (a), mPrP-b (b), mPrP-c (c), and mPrP-R (R) using either proteinase K (5A) or chymotrypsin (5B).

Proteolysis of mPrP(23-231)

mPrP(23-231) was digested using chymotrypsin and proteinase K in N-ethylmorpholin acetate (50 mM, pH 8.1) at 37° C. for 1 hour. The weight ratio of substrate to enzyme was in the range of 100:1 to 1000000:1 (10–0.001 µg/ml). The digestion reactions were terminated by addition of one to two volumes of 4% aqueous trifluoroacetic acid. The samples were then freeze-dried. The freeze-dried, treated samples were then analyzed by SDS-PAGE, as shown in FIG. 5.

mPrP-N and mPrP-z (1 mg/ml) were digested by proteinase K and a-chymotrypsin in 100 mM N-ethylmorpholine buffer (pH 8.1). The weight ratio of enzyme to protein ranges from 1/100 to 1/1000,000 (10–0.001 mg/ml). Digestion was carried out at 37° C. for 1 hour and was stopped by adding two volumes of 4% of trifluoroacetic acid. Digested samples were freeze-dried and analyzed by 15% SDS-PAGE.

Example 10

Determination of the Status of the Disulfide Bond

Both mPrP-N and mPrP-z were allowed to react with vinylpyridine with and without prior reduction. Reduction was performed at 23° C. for 90 min in the Tris-HCl buffer (0.1M, pH 8.0) containing 100 mM dithiothreitol and 8 M Urea. Modification with vinylpyridine was carried out in the same Tris-HCl buffer using an excess molar concentration of the reagent (0.2M) over dithiothreitol. Reaction with vinylpyridine was carried out at 23° C. for 45 min. Vinylpyridine modified samples were purified by reversed phase HPLC, freeze-dried and then analyzed by MALDI-TOF-MS.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein, but rather that the claims be construed as encompassing all the features of patentable novelty which reside in the present invention, including all features which would be treated as equivalents thereof by those skilled in the art to which this invention pertains.

All references cited in the present application, including journal articles, U.S. and foreign patents and patent applications, are herein incorporated by reference.

We claim:

1. An isolated prion peptide isoform having a sequence of at least a portion of a prion peptide wherein the isomer has a three-dimensional conformation isomeric to non-infectious cellular prion peptide.

2. The prion peptide isoform of claim 1 wherein said sequence comprises in the range of about 10 to about 254 amino acid residues.

3. The prion peptide isoform of claim 1 comprising a molecular weight in the range of about 20 kilodaltons to about 400 kilodaltons.

4. The prion peptide isoform or claim 3 wherein the isoform is a prion peptide polymer.

5. The prion peptide isoform or claim 1 wherein the three-dimensional conformation of said isoform comprises a greater proportion of β-sheet substructures than does the three dimensional conformation of said non-infectious cellular native prion peptide.

6. The prion peptide isoform or claim 1 wherein said isoform has greater resistance to proteolytic digestion than does the wild-type native prion peptide.

7. The prion peptide isoform of claim 1 wherein said isoform is less soluble than wild-type native prion peptide.

8. The prion peptide isoform of claim 1 wherein said isoform is encoded for by a mammalian prion sequence.

9. The prion peptide isoform of claim 1 wherein said isoform is at least partially purified.

10. A method for making a prion isomer, the method comprising the steps of:

a. incubating a prion peptide in a reducing buffer to yield a reduced prion peptide;

b. incubating said reduced prion peptide in folding buffer to yield a prion isomer wherein said folding buffer comprises urea at a concentration in the range of about 0.1M to 10M.

11. The method of claim 10 wherein said pH of said folding buffer is in the range of about 1.0 to about 5.0.

12. The method of claim 10 wherein said prion peptide comprises in the range of about 10 to about 254 amino acid residues.

13. The method of claim 10 wherein said prion peptide is a mammalian prion sequence.

14. The method of claim 10 wherein said isomer comprises a molecular weight in the range of about 20 kilodaltons to about 400 kilodaltons.

15. The method of claim 14 wherein said isomer is a polymer of at least a portion of non-infectious cellular prion.

16. The method of claim 10 further comprising the step of:

c. purifying said prion isomer peptide wherein said purifying comprises at least partially purifying said isomer.

17. A method for making a prion isomer, the method comprising the steps of:

a. incubating a prion peptide in a reducing buffer to yield a reduced prion peptide;

b. incubating said reduced prion peptide in folding buffer to yield a prion isomer peptide wherein said folding buffer comprises GdmCl at a concentration in the range of about 0.5M to 4.0M.

18. The method of claim 17 wherein the pH of said folding buffer is in the range of about 2.0 to about 6.0.

19. The method of claim 17 wherein said prion peptide comprises in the range of about 10 to about 254 amino acid residues.

20. The method of claim 19 wherein said prion peptide is a mammalian prion sequence.

21. The method of claim 17 wherein said isomer comprises a molecular weight in the range of about 20 kilodaltons to about 400 kilodaltons.

22. The method of claim 21 wherein said isomer is a polymer of at least a portion of non-infectious cellular prion.

23. The method of claim 21 further comprising the step of:

c. purifying said prion isomer peptide wherein said purifying comprises at least partially purifying said isomer.

24. A composition comprising an isolated prion peptide isomer having a sequence of at least a portion of wild type prion peptide and having a three-dimensional conformation isomeric to non-infectious cellular prion three-dimensional conformation.

25. The composition of claim 24 wherein said sequence comprises in the range of about 10 to about 254 amino acid residues.

26. The composition of claim 24 comprising a molecular weight in the range of about 20 kilodaltons to about 400 kilodaltons.

27. The composition of claim 26 wherein the isoform is a prion peptide polymer.

28. The composition of claim 24 wherein the three-dimensional conformation of said isoform comprises a greater proportion of β-sheet substructures than does the three dimensional conformation of said non-infectious cellular native prion peptide.

29. The composition of claim 24 wherein said isoform has greater resistance to proteolytic digestion than does the non-infectious cellular native prion peptide.

30. The composition of claim 24 wherein said isoform is less soluble than non-infectious cellular native prion peptide.

31. The composition of claim 24 wherein said isoform is encoded for by a mammalian prion sequence.

* * * * *

UNITED STATES PATENT AND TRADEMARK OFFICE
CERTIFICATE OF CORRECTION

PATENT NO. : 6,900,036 B2
APPLICATION NO. : 10/025976
DATED : May 31, 2005
INVENTOR(S) : Chang et al.

It is certified that error appears in the above-identified patent and that said Letters Patent is hereby corrected as shown below:

Column 20,
Line 48, delete "or" and insert -- of --, therefor.

Column 20,
Line 50, delete "or" and insert -- of --, therefor.

Column 20,
Line 55, delete "or" and insert -- of --, therefor.

Signed and Sealed this

Twenty-second Day of August, 2006

JON W. DUDAS
*Director of the United States Patent and Trademark Office*